United States Patent
Ganz et al.

(10) Patent No.: US 11,255,865 B2
(45) Date of Patent: Feb. 22, 2022

(54) IMMUNOASSAY FOR HUMAN ERYTHROFERRONE

(71) Applicant: The Regents of the University of California, Oakland, CA (US)

(72) Inventors: Tomas Ganz, Los Angeles, CA (US); Elizabeta Nemeth, Sherman Oaks, CA (US); Leon Kautz, Lacroix-Falgarde (FR); Chun-Ling Jung, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/619,140

(22) PCT Filed: May 28, 2018

(86) PCT No.: PCT/US2018/034797
§ 371 (c)(1),
(2) Date: Dec. 4, 2019

(87) PCT Pub. No.: WO2018/226441
PCT Pub. Date: Dec. 13, 2018

(65) Prior Publication Data
US 2020/0116741 A1    Apr. 16, 2020

Related U.S. Application Data

(60) Provisional application No. 62/515,679, filed on Jun. 6, 2017.

(51) Int. Cl.
*G01N 33/74* (2006.01)
*A61K 38/22* (2006.01)
*C07K 16/26* (2006.01)
*A61K 38/18* (2006.01)

(52) U.S. Cl.
CPC ........... *G01N 33/74* (2013.01); *A61K 38/22* (2013.01); *C07K 16/26* (2013.01); *A61K 38/1816* (2013.01); *C07K 2317/34* (2013.01)

(58) Field of Classification Search
None
See application file for complete search history.

(56) References Cited

U.S. PATENT DOCUMENTS

| | | |
|---|---|---|
| 2008/0226640 A1 | 9/2008 | Fitzgerald |
| 2009/0028784 A1 | 1/2009 | Garcia-Martinez |
| 2011/0045534 A1* | 2/2011 | Cheung ............... C07K 16/30 435/69.6 |
| 2012/0093837 A1 | 4/2012 | Gu |
| 2015/0337035 A1 | 11/2015 | Anderson |
| 2016/0122409 A1 | 5/2016 | Ganz |

FOREIGN PATENT DOCUMENTS

WO    2018027184 A1    2/2018

OTHER PUBLICATIONS

Vajdos et al. (J Mol Biol. Jul. 5, 2002;320(2):415-28 (Year: 2002).*
Zhao et al (Antibodies (Basel). Jun. 29, 2018;7(3):22) (Year: 2018).*
Brown et al. (J Immunol. May 1996;156(9):3285-91 (Year: 1996).*
Coffey & Ganz, "Erythroferrone: An Erythroid Regulator of Hepcidin and Iron Metabolism", Mar. 28, 2018, pp. e35, vol. 2, No. 2, Publisher: Hemasphere.
Extended European Search Report received in EP 18813831.7 dated Feb. 3, 2021.
Kautz et al., "Identification of erythroferrone as an erythroid regulator of iron metabolism", 2014, pp. 678-684, vol. 46, No. 7, Publisher: Nat Genet.
International Search Report received in PCT/US2018/034797 dated Oct. 17, 2018.
Written Opinion received in PCT/US2018/034797 dated Oct. 17, 2018.
Ganz et al., "Immunoassay for human serum erythroferrone", Sep. 7, 2017, pp. 1243-1246, vol. 130, No. 10, Publisher: Blood.
Han et al., "A Novel Dual Monoclonal Sandwich ELISA for Human Erythroferrone", Jan. 1, 2016, pp. 1272, vol. 128, No. 22, Publisher: Blood.
B4WSL5_SYNS7 Penicillin-binding Protein dimerisation domain family, Sep. 23, 2008, Publisher: UniProtKB.

* cited by examiner

*Primary Examiner* — Brian Gangle
*Assistant Examiner* — Andrea K McCollum
(74) *Attorney, Agent, or Firm* — Suzannah K. Sundby, Esq.; Canady + Lortz LLP

(57) ABSTRACT

Disclosed herein are antibodies that specifically bind human erythroferrone and assay methods for detecting and/or measuring human erythroferrone, analogs of human erythroferrone, and fragments thereof. Specifically, the methods comprising using an antibody as a capture reagent and an antibody as a detection reagent for detecting or measuring a detectable label of the at least one detection reagent bound to the erythroferrone polypeptide that is bound to the capture reagent. Further disclosed are the sequences of antibodies.

23 Claims, 3 Drawing Sheets
Specification includes a Sequence Listing.

SEQUENCE LISTING

<160> NUMBER OF SEQ ID NOS: 34

<210> SEQ ID NO 1
<211> LENGTH: 18
<212> TYPE: PRT
<213> ORGANISM: Artificial Sequence
<220> FEATURE:
<223> OTHER INFORMATION: Antigenic linear epitope of recombinant human erythroferrone

<400> SEQUENCE: 1

Glu Leu Pro Arg Gly Pro Gly Glu Ser Arg Ala Gly Pro Ala Ala Arg
1               5                   10                  15

Pro Pro

<210> SEQ ID NO 2
<211> LENGTH: 6
<212> TYPE: PRT
<213> ORGANISM: Artificial Sequence
<220> FEATURE:
<223> OTHER INFORMATION: Portion of antigenic linear epitope of recombinant human erythroferrone

<400> SEQUENCE: 2

Gly Glu Ser Arg Ala Gly
1               5

<210> SEQ ID NO 3
<211> LENGTH: 361
<212> TYPE: PRT
<213> ORGANISM: Artificial Sequence
<220> FEATURE:
<223> OTHER INFORMATION: Recombinant human erythroferrone with trypsin-sensitive site

<400> SEQUENCE: 3

Met Tyr Arg Met Gln Leu Leu Ser Cys Ile Ala Leu Ser Leu Ala Leu
1               5                   10                  15

Val Thr Asn Ser Ile Ser Ala Met Val Arg Ser Asp Tyr Lys Asp Asp
                20                  25                  30

Asp Asp Lys Ser Pro Glu Pro Gly Ala Pro Ser Arg Ser Arg Ala Arg
            35                  40                  45

Arg Glu Pro Pro Pro Gly Asn Glu Leu Pro Arg Gly Pro Gly Glu Ser
        50                  55                  60

Arg Ala Gly Pro Ala Ala Arg Pro Pro Glu Pro Thr Ala Glu Arg Ala
65                  70                  75                  80

His Ser Val Asp Pro Arg Asp Ala Trp Met Leu Phe Val Arg Gln Ser
                85                  90                  95

Asp Lys Gly Val Asn Gly Lys Lys Arg Ser Arg Gly Lys Ala Lys Lys
                100                 105                 110

Leu Lys Phe Gly Leu Pro Gly Pro Pro Gly Pro Pro Gly Pro Gln Gly
            115                 120                 125

Pro Pro Gly Pro Ile Ile Pro Pro Glu Ala Leu Leu Lys Glu Phe Gln
        130                 135                 140

Leu Leu Leu Lys Gly Ala Val Arg Gln Arg Glu Arg Ala Glu Pro Glu
145                 150                 155                 160

Pro Cys Thr Cys Gly Pro Ala Gly Pro Val Ala Ala Ser Leu Ala Pro
                165                 170                 175

Val Ser Ala Thr Ala Gly Glu Asp Asp Asp Val Gly Asp Val
                180                 185                 190

```
Leu Ala Leu Leu Ala Ala Pro Leu Ala Pro Gly Arg Ala Pro Arg
            195                 200                 205

Val Glu Ala Ala Phe Leu Cys Arg Leu Arg Asp Ala Leu Val Glu
    210                 215                 220

Arg Arg Ala Leu His Glu Leu Gly Val Tyr Tyr Leu Pro Asp Ala Glu
225                 230                 235                 240

Gly Ala Phe Arg Arg Gly Pro Gly Leu Asn Leu Thr Ser Gly Gln Tyr
                245                 250                 255

Arg Ala Pro Val Ala Gly Phe Tyr Ala Leu Ala Ala Thr Leu His Val
            260                 265                 270

Ala Leu Gly Glu Pro Pro Arg Arg Gly Pro Pro Arg Pro Arg Asp His
        275                 280                 285

Leu Arg Leu Leu Ile Cys Ile Gln Ser Arg Cys Gln Arg Asn Ala Ser
290                 295                 300

Leu Glu Ala Ile Met Gly Leu Glu Ser Ser Ser Glu Leu Phe Thr Ile
305                 310                 315                 320

Ser Val Asn Gly Val Leu Tyr Leu Gln Met Gly Gln Trp Thr Ser Val
                325                 330                 335

Phe Leu Asp Asn Ala Ser Gly Cys Ser Leu Thr Val Arg Ser Gly Ser
            340                 345                 350

His Phe Ser Ala Val Leu Leu Gly Val
        355                 360

<210> SEQ ID NO 4
<211> LENGTH: 5
<212> TYPE: PRT
<213> ORGANISM: Artificial Sequence
<220> FEATURE:
<223> OTHER INFORMATION: Spacer of recombinant human erythroferrone

<400> SEQUENCE: 4

Ala Met Val Arg Ser
1               5

<210> SEQ ID NO 5
<211> LENGTH: 8
<212> TYPE: PRT
<213> ORGANISM: Artificial Sequence
<220> FEATURE:
<223> OTHER INFORMATION: FLAG-tag of recombinant human erythroferrone

<400> SEQUENCE: 5

Asp Tyr Lys Asp Asp Asp Asp Lys
1               5

<210> SEQ ID NO 6
<211> LENGTH: 11
<212> TYPE: PRT
<213> ORGANISM: Artificial Sequence
<220> FEATURE:
<223> OTHER INFORMATION: Trypsin-sensitive site of recombinant human
      erythroferrone

<400> SEQUENCE: 6

Gly Ala Pro Ser Arg Ser Arg Ala Arg Arg Glu
1               5                   10

<210> SEQ ID NO 7
<211> LENGTH: 350
<212> TYPE: PRT
<213> ORGANISM: Artificial Sequence
<220> FEATURE:
```

<223> OTHER INFORMATION: Recombinant human erythroferrone without
      trypsin-sensitive site

<400> SEQUENCE: 7

| | | | | | | | | | | | | | | | |
|---|---|---|---|---|---|---|---|---|---|---|---|---|---|---|---|
| Met | Tyr | Arg | Met | Gln | Leu | Leu | Ser | Cys | Ile | Ala | Leu | Ser | Leu | Ala | Leu |
| 1 | | | | 5 | | | | | 10 | | | | | 15 | |
| Val | Thr | Asn | Ser | Ile | Ser | Ala | Met | Val | Arg | Ser | Asp | Tyr | Lys | Asp | Asp |
| | | | 20 | | | | | 25 | | | | | 30 | | |
| Asp | Asp | Lys | Ser | Pro | Glu | Pro | Pro | Pro | Gly | Asn | Glu | Leu | Pro | Arg | |
| | | 35 | | | | 40 | | | | 45 | | | | | |
| Gly | Pro | Gly | Glu | Ser | Arg | Ala | Gly | Pro | Ala | Ala | Arg | Pro | Pro | Glu | Pro |
| | 50 | | | | | 55 | | | | | 60 | | | | |
| Thr | Ala | Glu | Arg | Ala | His | Ser | Val | Asp | Pro | Arg | Asp | Ala | Trp | Met | Leu |
| 65 | | | | | 70 | | | | | 75 | | | | | 80 |
| Phe | Val | Arg | Gln | Ser | Asp | Lys | Gly | Val | Asn | Gly | Lys | Lys | Arg | Ser | Arg |
| | | | | 85 | | | | | 90 | | | | | 95 | |
| Gly | Lys | Ala | Lys | Lys | Leu | Lys | Phe | Gly | Leu | Pro | Gly | Pro | Pro | Gly | Pro |
| | | | 100 | | | | | 105 | | | | | 110 | | |
| Pro | Gly | Pro | Gln | Gly | Pro | Pro | Gly | Pro | Ile | Ile | Pro | Glu | Ala | Leu | |
| | | 115 | | | | 120 | | | | 125 | | | | | |
| Leu | Lys | Glu | Phe | Gln | Leu | Leu | Leu | Lys | Gly | Ala | Val | Arg | Gln | Arg | Glu |
| | 130 | | | | | 135 | | | | | 140 | | | | |
| Arg | Ala | Glu | Pro | Glu | Pro | Cys | Thr | Cys | Gly | Pro | Ala | Gly | Pro | Val | Ala |
| 145 | | | | | 150 | | | | | 155 | | | | | 160 |
| Ala | Ser | Leu | Ala | Pro | Val | Ser | Ala | Thr | Ala | Gly | Glu | Asp | Asp | Asp | |
| | | | | 165 | | | | | 170 | | | | | 175 | |
| Val | Val | Gly | Asp | Val | Leu | Ala | Leu | Leu | Ala | Ala | Pro | Leu | Ala | Pro | Gly |
| | | | 180 | | | | | 185 | | | | | 190 | | |
| Pro | Arg | Ala | Pro | Arg | Val | Glu | Ala | Ala | Phe | Leu | Cys | Arg | Leu | Arg | Arg |
| | | 195 | | | | 200 | | | | 205 | | | | | |
| Asp | Ala | Leu | Val | Glu | Arg | Arg | Ala | Leu | His | Glu | Leu | Gly | Val | Tyr | Tyr |
| | 210 | | | | | 215 | | | | | 220 | | | | |
| Leu | Pro | Asp | Ala | Glu | Gly | Ala | Phe | Arg | Arg | Gly | Pro | Gly | Leu | Asn | Leu |
| 225 | | | | | 230 | | | | | 235 | | | | | 240 |
| Thr | Ser | Gly | Gln | Tyr | Arg | Ala | Pro | Val | Ala | Gly | Phe | Tyr | Ala | Leu | Ala |
| | | | | 245 | | | | | 250 | | | | | 255 | |
| Ala | Thr | Leu | His | Val | Ala | Leu | Gly | Glu | Pro | Pro | Arg | Arg | Gly | Pro | Pro |
| | | | 260 | | | | | 265 | | | | | 270 | | |
| Arg | Pro | Arg | Asp | His | Leu | Arg | Leu | Leu | Ile | Cys | Ile | Gln | Ser | Arg | Cys |
| | | 275 | | | | 280 | | | | 285 | | | | | |
| Gln | Arg | Asn | Ala | Ser | Leu | Glu | Ala | Ile | Met | Gly | Leu | Glu | Ser | Ser | Ser |
| | 290 | | | | | 295 | | | | | 300 | | | | |
| Glu | Leu | Phe | Thr | Ile | Ser | Val | Asn | Gly | Val | Leu | Tyr | Leu | Gln | Met | Gly |
| 305 | | | | | 310 | | | | | 315 | | | | | 320 |
| Gln | Trp | Thr | Ser | Val | Phe | Leu | Asp | Asn | Ala | Ser | Gly | Cys | Ser | Leu | Thr |
| | | | | 325 | | | | | 330 | | | | | 335 | |
| Val | Arg | Ser | Gly | Ser | His | Phe | Ser | Ala | Val | Leu | Leu | Gly | Val | | |
| | | | 340 | | | | | 345 | | | | | 350 | | |

<210> SEQ ID NO 8
<211> LENGTH: 1374
<212> TYPE: DNA
<213> ORGANISM: Artificial Sequence
<220> FEATURE:
<223> OTHER INFORMATION: VH sequence of monoclonal antibody Mab#9
<220> FEATURE:

-continued

<221> NAME/KEY: CDS
<222> LOCATION: (1)..(1374)

<400> SEQUENCE: 8

| | | | | | | | | | | | | | | | | |
|---|---|---|---|---|---|---|---|---|---|---|---|---|---|---|---|---|
| atg | gag | act | ggg | ctg | cgc | tgg | ctt | ctc | ctg | gtc | gct | gtg | ctc | aaa | ggt | 48 |
| Met | Glu | Thr | Gly | Leu | Arg | Trp | Leu | Leu | Leu | Val | Ala | Val | Leu | Lys | Gly | |
| 1 | | | | 5 | | | | | 10 | | | | | 15 | | |
| gtc | cag | tgt | cag | tcg | gtg | gag | gag | tcc | ggg | ggt | cgc | ctg | gtc | acg | cct | 96 |
| Val | Gln | Cys | Gln | Ser | Val | Glu | Glu | Ser | Gly | Gly | Arg | Leu | Val | Thr | Pro | |
| | | | 20 | | | | | 25 | | | | | 30 | | | |
| ggg | aca | ccc | ctg | aca | ctc | acc | tgc | aca | gtc | tct | gga | atc | gac | ctc | aat | 144 |
| Gly | Thr | Pro | Leu | Thr | Leu | Thr | Cys | Thr | Val | Ser | Gly | Ile | Asp | Leu | Asn | |
| | | 35 | | | | | 40 | | | | | 45 | | | | |
| gac | aat | gca | atg | aga | tgg | gtc | cgc | cag | gct | ccc | ggg | aag | ggg | ctg | gaa | 192 |
| Asp | Asn | Ala | Met | Arg | Trp | Val | Arg | Gln | Ala | Pro | Gly | Lys | Gly | Leu | Glu | |
| 50 | | | | | 55 | | | | | 60 | | | | | | |
| tgg | atc | gga | gtc | att | tat | att | gat | aca | agc | aca | tac | tac | gcg | agc | tgg | 240 |
| Trp | Ile | Gly | Val | Ile | Tyr | Ile | Asp | Thr | Ser | Thr | Tyr | Tyr | Ala | Ser | Trp | |
| 65 | | | | | 70 | | | | | 75 | | | | | 80 | |
| gcg | aaa | ggc | cga | ttc | acc | atc | tcc | aaa | acc | tcg | tcg | acc | acg | gtg | gat | 288 |
| Ala | Lys | Gly | Arg | Phe | Thr | Ile | Ser | Lys | Thr | Ser | Ser | Thr | Thr | Val | Asp | |
| | | | | 85 | | | | | 90 | | | | | 95 | | |
| ctg | aaa | atc | acc | agt | ccg | aca | acc | gag | gac | acg | gcc | acc | tat | ttc | tgt | 336 |
| Leu | Lys | Ile | Thr | Ser | Pro | Thr | Thr | Glu | Asp | Thr | Ala | Thr | Tyr | Phe | Cys | |
| | | | 100 | | | | | 105 | | | | | 110 | | | |
| gtc | aga | gag | gat | ggt | tat | agg | ctt | ggt | gac | gtc | tgg | ggc | cca | ggc | acc | 384 |
| Val | Arg | Glu | Asp | Gly | Tyr | Arg | Leu | Gly | Asp | Val | Trp | Gly | Pro | Gly | Thr | |
| | | 115 | | | | | 120 | | | | | 125 | | | | |
| ctg | gtc | acc | gtc | tcc | tca | ggg | caa | cct | aag | gct | cca | tca | gtc | ttc | cca | 432 |
| Leu | Val | Thr | Val | Ser | Ser | Gly | Gln | Pro | Lys | Ala | Pro | Ser | Val | Phe | Pro | |
| | 130 | | | | | 135 | | | | | 140 | | | | | |
| ctg | gcc | ccc | tgc | tgc | ggg | gac | aca | ccc | agc | tcc | acg | gtg | acc | ctg | ggc | 480 |
| Leu | Ala | Pro | Cys | Cys | Gly | Asp | Thr | Pro | Ser | Ser | Thr | Val | Thr | Leu | Gly | |
| 145 | | | | | 150 | | | | | 155 | | | | | 160 | |
| tgc | ctg | gtc | aaa | ggg | tac | ctc | ccg | gag | cca | gtg | acc | gtg | acc | tgg | aac | 528 |
| Cys | Leu | Val | Lys | Gly | Tyr | Leu | Pro | Glu | Pro | Val | Thr | Val | Thr | Trp | Asn | |
| | | | | 165 | | | | | 170 | | | | | 175 | | |
| tcg | ggc | acc | ctc | acc | aat | ggg | gta | cgc | acc | ttc | ccg | tcc | gtc | cgg | cag | 576 |
| Ser | Gly | Thr | Leu | Thr | Asn | Gly | Val | Arg | Thr | Phe | Pro | Ser | Val | Arg | Gln | |
| | | | 180 | | | | | 185 | | | | | 190 | | | |
| tcc | tca | ggc | ctc | tac | tcg | ctg | agc | agc | gtg | gtg | agc | gtg | acc | tca | agc | 624 |
| Ser | Ser | Gly | Leu | Tyr | Ser | Leu | Ser | Ser | Val | Val | Ser | Val | Thr | Ser | Ser | |
| | | 195 | | | | | 200 | | | | | 205 | | | | |
| agc | cag | ccc | gtc | acc | tgc | aac | gtg | gcc | cac | cca | gcc | acc | aac | acc | aaa | 672 |
| Ser | Gln | Pro | Val | Thr | Cys | Asn | Val | Ala | His | Pro | Ala | Thr | Asn | Thr | Lys | |
| | | | 210 | | | | | 215 | | | | | 220 | | | |
| gtg | gac | aag | acc | gtt | gcg | ccc | tcg | aca | tgc | agc | aag | ccc | acg | tgc | cca | 720 |
| Val | Asp | Lys | Thr | Val | Ala | Pro | Ser | Thr | Cys | Ser | Lys | Pro | Thr | Cys | Pro | |
| 225 | | | | | 230 | | | | | 235 | | | | | 240 | |
| ccc | cct | gaa | ctc | ctg | ggg | gga | ccg | tct | gtc | ttc | atc | ttc | ccc | cca | aaa | 768 |
| Pro | Pro | Glu | Leu | Leu | Gly | Gly | Pro | Ser | Val | Phe | Ile | Phe | Pro | Pro | Lys | |
| | | | | 245 | | | | | 250 | | | | | 255 | | |
| ccc | aag | gac | acc | ctc | atg | atc | tca | cgc | acc | ccc | gag | gtc | aca | tgc | gtg | 816 |
| Pro | Lys | Asp | Thr | Leu | Met | Ile | Ser | Arg | Thr | Pro | Glu | Val | Thr | Cys | Val | |
| | | | 260 | | | | | 265 | | | | | 270 | | | |
| gtg | gtg | gac | gtg | agc | cag | gat | gac | ccc | gag | gtg | cag | ttc | aca | tgg | tac | 864 |
| Val | Val | Asp | Val | Ser | Gln | Asp | Asp | Pro | Glu | Val | Gln | Phe | Thr | Trp | Tyr | |
| | | 275 | | | | | 280 | | | | | 285 | | | | |
| ata | aac | aac | gag | cag | gtg | cgc | acc | gcc | cgg | ccg | ccg | cta | cgg | gag | cag | 912 |
| Ile | Asn | Asn | Glu | Gln | Val | Arg | Thr | Ala | Arg | Pro | Pro | Leu | Arg | Glu | Gln | |

```
                    290                 295                 300
cag ttc aac agc acg atc cgc gtg gtc agc acc ctc ccc atc gcg cac        960
Gln Phe Asn Ser Thr Ile Arg Val Val Ser Thr Leu Pro Ile Ala His
305                 310                 315                 320 cag gac tgg ctg agg ggc aag gag ttc aag tgc aaa gtc cac aac aag       1008
Gln Asp Trp Leu Arg Gly Lys Glu Phe Lys Cys Lys Val His Asn Lys
            325                 330                 335 gca ctc ccg gcc ccc atc gag aaa acc atc tcc aaa gcc aga ggg cag       1056
Ala Leu Pro Ala Pro Ile Glu Lys Thr Ile Ser Lys Ala Arg Gly Gln
        340                 345                 350 ccc ctg gag ccg aag gtc tac acc atg ggc cct ccc cgg gag gag ctg       1104
Pro Leu Glu Pro Lys Val Tyr Thr Met Gly Pro Pro Arg Glu Glu Leu
    355                 360                 365 agc agc agg tcg gtc agc ctg acc tgc atg atc aac ggc ttc tac cct       1152
Ser Ser Arg Ser Val Ser Leu Thr Cys Met Ile Asn Gly Phe Tyr Pro
370                 375                 380 tcc gac atc tcg gtg gag tgg gag aag aac ggg aag gca gag gac aac       1200
Ser Asp Ile Ser Val Glu Trp Glu Lys Asn Gly Lys Ala Glu Asp Asn
385                 390                 395                 400 tac aag acc acg ccg gcc gtg ctg gac agc gac ggc tcc tac ttc ctc       1248
Tyr Lys Thr Thr Pro Ala Val Leu Asp Ser Asp Gly Ser Tyr Phe Leu
            405                 410                 415 tac agc aag ctc tca gtg ccc acg agt gag tgg cag cgg ggc gac gtc       1296
Tyr Ser Lys Leu Ser Val Pro Thr Ser Glu Trp Gln Arg Gly Asp Val
        420                 425                 430 ttc acc tgc tcc gtg atg cac gag gcc ttg cac aac cac tac acg cag       1344
Phe Thr Cys Ser Val Met His Glu Ala Leu His Asn His Tyr Thr Gln
    435                 440                 445 aag tcc atc tcc cgc tct ccg ggt aaa tga                               1374
Lys Ser Ile Ser Arg Ser Pro Gly Lys
450                 455

<210> SEQ ID NO 9
<211> LENGTH: 457
<212> TYPE: PRT
<213> ORGANISM: Artificial Sequence
<220> FEATURE:
<223> OTHER INFORMATION: Synthetic Construct

<400> SEQUENCE: 9

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Asn
        35                  40                  45

Asp Asn Ala Met Arg Trp Val Arg Gln Ala Pro Gly Lys Gly Leu Glu
    50                  55                  60

Trp Ile Gly Val Ile Tyr Ile Asp Thr Ser Thr Tyr Tyr Ala Ser Trp
65                  70                  75                  80

Ala Lys Gly Arg Phe Thr Ile Ser Lys Thr Ser Ser Thr Thr Val Asp
                85                  90                  95

Leu Lys Ile Thr Ser Pro Thr Thr Glu Asp Thr Ala Thr Tyr Phe Cys
            100                 105                 110

Val Arg Glu Asp Gly Tyr Arg Leu Gly Asp Val Trp Gly Pro Gly Thr
        115                 120                 125

Leu Val Thr Val Ser Ser Gly Gln Pro Lys Ala Pro Ser Val Phe Pro
    130                 135                 140
```

```
Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
            165                 170                 175

Ser Gly Thr Leu Thr Asn Gly Val Arg Thr Phe Pro Ser Val Arg Gln
                180                 185                 190

Ser Ser Gly Leu Tyr Ser Leu Ser Ser Val Val Ser Val Thr Ser Ser
            195                 200                 205

Ser Gln Pro Val Thr Cys Asn Val Ala His Pro Ala Thr Asn Thr Lys
        210                 215                 220

Val Asp Lys Thr Val Ala Pro Ser Thr Cys Ser Lys Pro Thr Cys Pro
225                 230                 235                 240

Pro Pro Glu Leu Leu Gly Gly Pro Ser Val Phe Ile Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Asp Asp Pro Glu Val Gln Phe Thr Trp Tyr
        275                 280                 285

Ile Asn Asn Glu Gln Val Arg Thr Ala Arg Pro Pro Leu Arg Glu Gln
290                 295                 300

Gln Phe Asn Ser Thr Ile Arg Val Val Ser Thr Leu Pro Ile Ala His
305                 310                 315                 320

Gln Asp Trp Leu Arg Gly Lys Glu Phe Lys Cys Lys Val His Asn Lys
                325                 330                 335

Ala Leu Pro Ala Pro Ile Glu Lys Thr Ile Ser Lys Ala Arg Gly Gln
            340                 345                 350

Pro Leu Glu Pro Lys Val Tyr Thr Met Gly Pro Pro Arg Glu Glu Leu
        355                 360                 365

Ser Ser Arg Ser Val Ser Leu Thr Cys Met Ile Asn Gly Phe Tyr Pro
370                 375                 380

Ser Asp Ile Ser Val Glu Trp Glu Lys Asn Gly Lys Ala Glu Asp Asn
385                 390                 395                 400

Tyr Lys Thr Thr Pro Ala Val Leu Asp Ser Asp Gly Ser Tyr Phe Leu
                405                 410                 415

Tyr Ser Lys Leu Ser Val Pro Thr Ser Glu Trp Gln Arg Gly Asp Val
            420                 425                 430

Phe Thr Cys Ser Val Met His Glu Ala Leu His Asn His Tyr Thr Gln
        435                 440                 445

Lys Ser Ile Ser Arg Ser Pro Gly Lys
450                 455

<210> SEQ ID NO 10
<211> LENGTH: 8
<212> TYPE: PRT
<213> ORGANISM: Artificial Sequence
<220> FEATURE:
<223> OTHER INFORMATION: Predicted CDR1 of VH sequence of monoclonal
      antibody Mab#9

<400> SEQUENCE: 10

Gly Ile Asp Leu Asn Asp Asn Ala
1               5

<210> SEQ ID NO 11
<211> LENGTH: 7
<212> TYPE: PRT
<213> ORGANISM: Artificial Sequence
```

<220> FEATURE:
<223> OTHER INFORMATION: Predicted CDR2 of VH sequence of monoclonal antibody Mab#9

<400> SEQUENCE: 11

Ile Tyr Ile Asp Thr Ser Thr
1               5

<210> SEQ ID NO 12
<211> LENGTH: 11
<212> TYPE: PRT
<213> ORGANISM: Artificial Sequence
<220> FEATURE:
<223> OTHER INFORMATION: Predicted CDR3 VH sequence of monoclonal antibody Mab#9

<400> SEQUENCE: 12

Val Arg Glu Asp Gly Tyr Arg Leu Gly Asp Val
1               5                   10

<210> SEQ ID NO 13
<211> LENGTH: 717
<212> TYPE: DNA
<213> ORGANISM: Artificial Sequence
<220> FEATURE:
<223> OTHER INFORMATION: VL sequence of monoclonal antibody Mab#9
<220> FEATURE:
<221> NAME/KEY: CDS
<222> LOCATION: (1)..(717)

<400> SEQUENCE: 13

```
atg gac acg agg gcc ccc act cag ctg ctg ggg ctc ctg ctg ctc tgg       48
Met Asp Thr Arg Ala Pro Thr Gln Leu Leu Gly Leu Leu Leu Leu Trp
1               5                   10                  15 ctc cca gat gcc aga tgt gcg ctt gtg atg acc cag act cca tcc tcc       96
Leu Pro Asp Ala Arg Cys Ala Leu Val Met Thr Gln Thr Pro Ser Ser
            20                  25                  30 gtg tct gca ggt gtg gga ggc aca gtc acc atc aac tgc cag gcc agt      144
Val Ser Ala Gly Val Gly Gly Thr Val Thr Ile Asn Cys Gln Ala Ser
        35                  40                  45 cag agt ctt tat aat aac aac tat tta tcc tgg ttt cag cag aaa cca      192
Gln Ser Leu Tyr Asn Asn Asn Tyr Leu Ser Trp Phe Gln Gln Lys Pro
    50                  55                  60 ggg cag cct ccc aag ctc ctg atc tac tgg gca tcc act ctg gca tct      240
Gly Gln Pro Pro Lys Leu Leu Ile Tyr Trp Ala Ser Thr Leu Ala Ser
65                  70                  75                  80 ggg gtc cca tcc cgg ttc agt ggc agt gga tct ggg aca cag ttc act      288
Gly Val Pro Ser Arg Phe Ser Gly Ser Gly Ser Gly Thr Gln Phe Thr
                85                  90                  95 ctc acc atc agt ggc gtg gcg tgt gac gat gct gcc act tac tac tgt      336
Leu Thr Ile Ser Gly Val Ala Cys Asp Asp Ala Ala Thr Tyr Tyr Cys
            100                 105                 110 gca ggc tat aaa agt agt agt aat gat gat ttt gct ttc ggc gga ggg      384
Ala Gly Tyr Lys Ser Ser Ser Asn Asp Asp Phe Ala Phe Gly Gly Gly
        115                 120                 125 acc gag gtg gtg gtc aaa ggt gat cca gtt gca cct act gtc ctc atc      432
Thr Glu Val Val Val Lys Gly Asp Pro Val Ala Pro Thr Val Leu Ile
    130                 135                 140 ttc cca cca gct gct gat cag gtg gca act gga aca gtc acc atc gtg      480
Phe Pro Pro Ala Ala Asp Gln Val Ala Thr Gly Thr Val Thr Ile Val
145                 150                 155                 160 tgt gtg gcg aat aaa tac ttt ccc gat gtc acc gtc acc tgg gag gtg      528
Cys Val Ala Asn Lys Tyr Phe Pro Asp Val Thr Val Thr Trp Glu Val
                165                 170                 175
```

```
gat ggc acc acc caa aca act ggc atc gag aac cgt aaa aca ccg cag    576
Asp Gly Thr Thr Gln Thr Thr Gly Ile Glu Asn Arg Lys Thr Pro Gln
        180                 185                 190 aat tct gca gat tgt acc tac aac ctc agc agc act ctg aca ctg acc    624
Asn Ser Ala Asp Cys Thr Tyr Asn Leu Ser Ser Thr Leu Thr Leu Thr
    195                 200                 205 agc aca cag tac aac agc cac aaa gag tac acc tgc aag gtg acc cag    672
Ser Thr Gln Tyr Asn Ser His Lys Glu Tyr Thr Cys Lys Val Thr Gln
210                 215                 220 ggc acg acc tca gtc gtc cag agc ttc aat agg ggt gac tgt tag        717
Gly Thr Thr Ser Val Val Gln Ser Phe Asn Arg Gly Asp Cys
225                 230                 235

<210> SEQ ID NO 14
<211> LENGTH: 238
<212> TYPE: PRT
<213> ORGANISM: Artificial Sequence
<220> FEATURE:
<223> OTHER INFORMATION: Synthetic Construct

<400> SEQUENCE: 14

Met Asp Thr Arg Ala Pro Thr Gln Leu Leu Gly Leu Leu Leu Leu Trp
1               5                   10                  15

Leu Pro Asp Ala Arg Cys Ala Leu Val Met Thr Gln Thr Pro Ser Ser
            20                  25                  30

Val Ser Ala Gly Val Gly Gly Thr Val Thr Ile Asn Cys Gln Ala Ser
        35                  40                  45

Gln Ser Leu Tyr Asn Asn Asn Tyr Leu Ser Trp Phe Gln Gln Lys Pro
    50                  55                  60

Gly Gln Pro Pro Lys Leu Leu Ile Tyr Trp Ala Ser Thr Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Gly Val Ala Cys Asp Asp Ala Ala Thr Tyr Tyr Cys
            100                 105                 110

Ala Gly Tyr Lys Ser Ser Ser Asn Asp Asp Phe Ala Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Arg Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235

<210> SEQ ID NO 15
<211> LENGTH: 8
<212> TYPE: PRT
<213> ORGANISM: Artificial Sequence
<220> FEATURE:
<223> OTHER INFORMATION: Predicted CDR1 of VL sequence of monoclonal
``` antibody Mab#9

<400> SEQUENCE: 15

Gln Ser Leu Tyr Asn Asn Tyr
1               5

<210> SEQ ID NO 16
<211> LENGTH: 3
<212> TYPE: PRT
<213> ORGANISM: Artificial Sequence
<220> FEATURE:
<223> OTHER INFORMATION: Predicted CDR2 of VL sequence of monoclonal
      antibody Mab#9

<400> SEQUENCE: 16

Trp Ala Ser
1

<210> SEQ ID NO 17
<211> LENGTH: 12
<212> TYPE: PRT
<213> ORGANISM: Artificial Sequence
<220> FEATURE:
<223> OTHER INFORMATION: Predicted CDR3 of VL sequence of monoclonal
      antibody Mab#9

<400> SEQUENCE: 17

Ala Gly Tyr Lys Ser Ser Ser Asn Asp Asp Phe Ala
1               5                   10

<210> SEQ ID NO 18
<211> LENGTH: 1383
<212> TYPE: DNA
<213> ORGANISM: Artificial Sequence
<220> FEATURE:
<223> OTHER INFORMATION: VH sequence of monoclonal antibody Mab#42
<220> FEATURE:
<221> NAME/KEY: CDS
<222> LOCATION: (1)..(1383)

<400> SEQUENCE: 18

```
atg gag act ggg ctg cgc tgg ctt ctc ctg gtc gct gtg ctc aaa ggt        48
Met Glu Thr Gly Leu Arg Trp Leu Leu Leu Val Ala Val Leu Lys Gly
1               5                   10                  15 gcc cag tgc cag tcg ctg gag gag tcc ggg ggt cgc ctg gta acg cct        96
Ala Gln Cys Gln Ser Leu Glu Glu Ser Gly Gly Arg Leu Val Thr Pro
                20                  25                  30 gga gga tcc ctg aca ctc acc tgc aca gtc tct gga atc gac ctc agt       144
Gly Gly Ser Leu Thr Leu Thr Cys Thr Val Ser Gly Ile Asp Leu Ser
            35                  40                  45 agc tat gaa atg ggc tgg gtc cgc cag gct cca ggg aag ggg ctg gaa       192
Ser Tyr Glu Met Gly Trp Val Arg Gln Ala Pro Gly Lys Gly Leu Glu
        50                  55                  60 tgg atc gga gta att ggt act gat ggt acc gca gtc tac gcg acc tgg       240
Trp Ile Gly Val Ile Gly Thr Asp Gly Thr Ala Val Tyr Ala Thr Trp
65                  70                  75                  80 gtg aaa ggc cga ttc acc atc tcc aaa acc tcg acc acg gtg gat ctg       288
Val Lys Gly Arg Phe Thr Ile Ser Lys Thr Ser Thr Thr Val Asp Leu
                85                  90                  95 aaa atg acc agt ctg aca acc gag gac acg gcc acc tat ttc tgt gcc       336
Lys Met Thr Ser Leu Thr Thr Glu Asp Thr Ala Thr Tyr Phe Cys Ala
                100                 105                 110 cga gat tct tct ggt aat agt aat tat agg gct ttt gat ccc tgg ggc       384
Arg Asp Ser Ser Gly Asn Ser Asn Tyr Arg Ala Phe Asp Pro Trp Gly
            115                 120                 125
```

```
cca ggc acc ctg gtc acc gtc tcc tca ggg caa cct aag gct cca tca      432
Pro Gly Thr Leu Val Thr Val Ser Ser Gly Gln Pro Lys Ala Pro Ser
    130             135             140 gtc ttc cca ctg gcc ccc tgc tgc ggg gac aca ccc agc tcc acg gtg      480
Val Phe Pro Leu Ala Pro Cys Cys Gly Asp Thr Pro Ser Ser Thr Val
145             150             155             160 acc ctg ggc tgc ctg gtc aaa ggg tac ctc ccg gag cca gtg acc gtg      528
Thr Leu Gly Cys Leu Val Lys Gly Tyr Leu Pro Glu Pro Val Thr Val
                165             170             175 acc tgg aac tcg ggc acc ctc acc aat ggg gta cgc acc ttc ccg tcc      576
Thr Trp Asn Ser Gly Thr Leu Thr Asn Gly Val Arg Thr Phe Pro Ser
            180             185             190 gtc cgg cag tcc tca ggc ctc tac tcg ctg agc agc gtg gtg agc gtg      624
Val Arg Gln Ser Ser Gly Leu Tyr Ser Leu Ser Ser Val Val Ser Val
        195             200             205 acc tca agc agc cag ccc gtc acc tgc aac gtg gcc cac cca gcc acc      672
Thr Ser Ser Ser Gln Pro Val Thr Cys Asn Val Ala His Pro Ala Thr
    210             215             220 aac acc aaa gtg gac aag acc gtt gcg ccc tcg aca tgc agc aag ccc      720
Asn Thr Lys Val Asp Lys Thr Val Ala Pro Ser Thr Cys Ser Lys Pro
225             230             235             240 acg tgc cca ccc cct gaa ctc ctg ggg gga ccg tct gtc ttc atc ttc      768
Thr Cys Pro Pro Pro Glu Leu Leu Gly Gly Pro Ser Val Phe Ile Phe
                245             250             255 ccc cca aaa ccc aag gac acc ctc atg atc tca cgc acc ccc gag gtc      816
Pro Pro Lys Pro Lys Asp Thr Leu Met Ile Ser Arg Thr Pro Glu Val
            260             265             270 aca tgc gtg gtg gtg gac gtg agc cag gat gac ccc gag gtg cag ttc      864
Thr Cys Val Val Val Asp Val Ser Gln Asp Asp Pro Glu Val Gln Phe
        275             280             285 aca tgg tac ata aac aac gag cag gtg cgc acc gcc cgg ccg ccg cta      912
Thr Trp Tyr Ile Asn Asn Glu Gln Val Arg Thr Ala Arg Pro Pro Leu
    290             295             300 cgg gag cag cag ttc aac agc acg atc cgc gtg gtc agc acc ctc ccc      960
Arg Glu Gln Gln Phe Asn Ser Thr Ile Arg Val Val Ser Thr Leu Pro
305             310             315             320 atc gcg cac cag gac tgg ctg agg ggc aag gag ttc aag tgc aaa gtc     1008
Ile Ala His Gln Asp Trp Leu Arg Gly Lys Glu Phe Lys Cys Lys Val
                325             330             335 cac aac aag gca ctc ccg gcc ccc atc gag aaa acc atc tcc aaa gcc     1056
His Asn Lys Ala Leu Pro Ala Pro Ile Glu Lys Thr Ile Ser Lys Ala
            340             345             350 aga ggg cag ccc ctg gag ccg aag gtc tac acc atg ggc cct ccc cgg     1104
Arg Gly Gln Pro Leu Glu Pro Lys Val Tyr Thr Met Gly Pro Pro Arg
        355             360             365 gag gag ctg agc agc agg tcg gtc agc ctg acc tgc atg atc aac ggc     1152
Glu Glu Leu Ser Ser Arg Ser Val Ser Leu Thr Cys Met Ile Asn Gly
    370             375             380 ttc tac cct tcc gac atc tcg gtg gag tgg gag aag aac ggg aag gca     1200
Phe Tyr Pro Ser Asp Ile Ser Val Glu Trp Glu Lys Asn Gly Lys Ala
385             390             395             400 gag gac aac tac aag acc acg ccg gcc gtg ctg gac agc gac ggc tcc     1248
Glu Asp Asn Tyr Lys Thr Thr Pro Ala Val Leu Asp Ser Asp Gly Ser
                405             410             415 tac ttc ctc tac agc aag ctc tca gtg ccc acg agt gag tgg cag cgg     1296
Tyr Phe Leu Tyr Ser Lys Leu Ser Val Pro Thr Ser Glu Trp Gln Arg
            420             425             430 ggc gac gtc ttc acc tgc tcc gtg atg cac gag gcc ttg cac aac cac     1344
Gly Asp Val Phe Thr Cys Ser Val Met His Glu Ala Leu His Asn His
```

```
                435                 440                 445
tac acg cag aag tcc atc tcc cgc tct ccg ggt aaa tga                1383
Tyr Thr Gln Lys Ser Ile Ser Arg Ser Pro Gly Lys
    450                 455                 460

<210> SEQ ID NO 19
<211> LENGTH: 460
<212> TYPE: PRT
<213> ORGANISM: Artificial Sequence
<220> FEATURE:
<223> OTHER INFORMATION: Synthetic Construct

<400> SEQUENCE: 19

Met Glu Thr Gly Leu Arg Trp Leu Leu Leu Val Ala Val Leu Lys Gly
1               5                   10                  15

Ala Gln Cys Gln Ser Leu Glu Glu Ser Gly Gly Arg Leu Val Thr Pro
            20                  25                  30

Gly Gly Ser Leu Thr Leu Thr Cys Thr Val Ser Gly Ile Asp Leu Ser
        35                  40                  45

Ser Tyr Glu Met Gly Trp Val Arg Gln Ala Pro Gly Lys Gly Leu Glu
    50                  55                  60

Trp Ile Gly Val Ile Gly Thr Asp Gly Thr Ala Val Tyr Ala Thr Trp
65                  70                  75                  80

Val Lys Gly Arg Phe Thr Ile Ser Lys Thr Ser Thr Thr Val Asp Leu
                85                  90                  95

Lys Met Thr Ser Leu Thr Thr Glu Asp Thr Ala Thr Tyr Phe Cys Ala
            100                 105                 110

Arg Asp Ser Ser Gly Asn Ser Asn Tyr Arg Ala Phe Asp Pro Trp Gly
        115                 120                 125

Pro Gly Thr Leu Val Thr Val Ser Ser Gly Gln Pro Lys Ala Pro Ser
    130                 135                 140

Val Phe Pro Leu Ala Pro Cys Cys Gly Asp Thr Pro Ser Ser Thr Val
145                 150                 155                 160

Thr Leu Gly Cys Leu Val Lys Gly Tyr Leu Pro Glu Pro Val Thr Val
                165                 170                 175

Thr Trp Asn Ser Gly Thr Leu Thr Asn Gly Val Arg Thr Phe Pro Ser
            180                 185                 190

Val Arg Gln Ser Ser Gly Leu Tyr Ser Leu Ser Ser Val Val Ser Val
        195                 200                 205

Thr Ser Ser Ser Gln Pro Val Thr Cys Asn Val Ala His Pro Ala Thr
    210                 215                 220

Asn Thr Lys Val Asp Lys Thr Val Ala Pro Ser Thr Cys Ser Lys Pro
225                 230                 235                 240

Thr Cys Pro Pro Pro Glu Leu Leu Gly Gly Pro Ser Val Phe Ile Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Asp Asp Pro Glu Val Gln Phe
        275                 280                 285

Thr Trp Tyr Ile Asn Asn Glu Gln Val Arg Thr Ala Arg Pro Pro Leu
    290                 295                 300

Arg Glu Gln Gln Phe Asn Ser Thr Ile Arg Val Val Ser Thr Leu Pro
305                 310                 315                 320

Ile Ala His Gln Asp Trp Leu Arg Gly Lys Glu Phe Lys Cys Lys Val
                325                 330                 335
```

```
His Asn Lys Ala Leu Pro Ala Pro Ile Glu Lys Thr Ile Ser Lys Ala
                340                 345                 350

Arg Gly Gln Pro Leu Glu Pro Lys Val Tyr Thr Met Gly Pro Pro Arg
            355                 360                 365

Glu Glu Leu Ser Ser Arg Ser Val Ser Leu Thr Cys Met Ile Asn Gly
        370                 375                 380

Phe Tyr Pro Ser Asp Ile Ser Val Glu Trp Glu Lys Asn Gly Lys Ala
385                 390                 395                 400

Glu Asp Asn Tyr Lys Thr Thr Pro Ala Val Leu Asp Ser Asp Gly Ser
                405                 410                 415

Tyr Phe Leu Tyr Ser Lys Leu Ser Val Pro Thr Ser Glu Trp Gln Arg
            420                 425                 430

Gly Asp Val Phe Thr Cys Ser Val Met His Glu Ala Leu His Asn His
        435                 440                 445

Tyr Thr Gln Lys Ser Ile Ser Arg Ser Pro Gly Lys
            450                 455                 460

<210> SEQ ID NO 20
<211> LENGTH: 8
<212> TYPE: PRT
<213> ORGANISM: Artificial Sequence
<220> FEATURE:
<223> OTHER INFORMATION: Predicted CDR1 of VH sequence of monoclonal
      antibody Mab#42

<400> SEQUENCE: 20

Gly Ile Asp Leu Ser Ser Tyr Glu
1               5

<210> SEQ ID NO 21
<211> LENGTH: 7
<212> TYPE: PRT
<213> ORGANISM: Artificial Sequence
<220> FEATURE:
<223> OTHER INFORMATION: Predicted CDR2 of VH sequence of monoclonal
      antibody Mab#42

<400> SEQUENCE: 21

Ile Gly Thr Asp Gly Thr Ala
1               5

<210> SEQ ID NO 22
<211> LENGTH: 15
<212> TYPE: PRT
<213> ORGANISM: Artificial Sequence
<220> FEATURE:
<223> OTHER INFORMATION: Predicted CDR3 of VH sequence of monoclonal
      antibody Mab#42

<400> SEQUENCE: 22

Ala Arg Asp Ser Ser Gly Asn Ser Asn Tyr Arg Ala Phe Asp Pro
1               5                   10                  15

<210> SEQ ID NO 23
<211> LENGTH: 711
<212> TYPE: DNA
<213> ORGANISM: Artificial Sequence
<220> FEATURE:
<223> OTHER INFORMATION: VL sequence of monoclonal antibody Mab#42
<220> FEATURE:
<221> NAME/KEY: CDS
<222> LOCATION: (1)..(711)

<400> SEQUENCE: 23
```

```
atg gac acg agg gcc ccc act cag ctg ctg ggg ctc ctg ctg ctc tgg      48
Met Asp Thr Arg Ala Pro Thr Gln Leu Leu Gly Leu Leu Leu Leu Trp
1               5                   10                  15 ctc cca ggt gcc aga tgt gcc tat gat atg acc cag act cca gcc tct      96
Leu Pro Gly Ala Arg Cys Ala Tyr Asp Met Thr Gln Thr Pro Ala Ser
            20                  25                  30 gtg gag gta gct gtg gga ggc aca gtc acc atc aag tgc cag gcc agt     144
Val Glu Val Ala Val Gly Gly Thr Val Thr Ile Lys Cys Gln Ala Ser
        35                  40                  45 cag agc att tac agc tac tta tcc tgg tat cag cag aaa cca ggg cag     192
Gln Ser Ile Tyr Ser Tyr Leu Ser Trp Tyr Gln Gln Lys Pro Gly Gln
    50                  55                  60 cct ccc aag ctc ctg atc tac agg gca tcc act ctg gca tct ggg gtc     240
Pro Pro Lys Leu Leu Ile Tyr Arg Ala Ser Thr Leu Ala Ser Gly Val
65                  70                  75                  80 cca tcg cgg ttc aaa ggc agt gga tct ggg aca cag ttc act ctc acc     288
Pro Ser Arg Phe Lys Gly Ser Gly Ser Gly Thr Gln Phe Thr Leu Thr
                85                  90                  95 ata agc gac ctg gag tgt gcc gat gct gcc act tac tac tgt caa cag     336
Ile Ser Asp Leu Glu Cys Ala Asp Ala Ala Thr Tyr Tyr Cys Gln Gln
            100                 105                 110 ggt ttt gtt att agt aat gtt ctt aat tct ttc ggc gga ggg acc gag     384
Gly Phe Val Ile Ser Asn Val Leu Asn Ser Phe Gly Gly Gly Thr Glu
        115                 120                 125 gtg gtg gtc aaa ggt gat cca gtt gca cct act gtc ctc atc ttc cca     432
Val Val Val Lys Gly Asp Pro Val Ala Pro Thr Val Leu Ile Phe Pro
    130                 135                 140 cca gct gct gat cag gtg gca act gga aca gtc acc atc gtg tgt gtg     480
Pro Ala Ala Asp Gln Val Ala Thr Gly Thr Val Thr Ile Val Cys Val
145                 150                 155                 160 gcg aat aaa tac ttt ccc gat gtc acc gtc acc tgg gag gtg gat ggc     528
Ala Asn Lys Tyr Phe Pro Asp Val Thr Val Thr Trp Glu Val Asp Gly
                165                 170                 175 acc acc caa aca act ggc atc gag aac agt aaa aca ccg cag aat tct     576
Thr Thr Gln Thr Thr Gly Ile Glu Asn Ser Lys Thr Pro Gln Asn Ser
            180                 185                 190 gca gat tgt acc tac aac ctc agc agc act ctg aca ctg acc agc aca     624
Ala Asp Cys Thr Tyr Asn Leu Ser Ser Thr Leu Thr Leu Thr Ser Thr
        195                 200                 205 cag tac aac agc cac aaa gag tac acc tgc aag gtg acc cag ggc acg     672
Gln Tyr Asn Ser His Lys Glu Tyr Thr Cys Lys Val Thr Gln Gly Thr
    210                 215                 220 acc tca gtc gtc cag agc ttc aat agg ggt gac tgt tag                 711
Thr Ser Val Val Gln Ser Phe Asn Arg Gly Asp Cys
225                 230                 235

<210> SEQ ID NO 24
<211> LENGTH: 236
<212> TYPE: PRT
<213> ORGANISM: Artificial Sequence
<220> FEATURE:
<223> OTHER INFORMATION: Synthetic Construct

<400> SEQUENCE: 24

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45
```

```
Gln Ser Ile Tyr Ser Tyr Leu Ser Trp Tyr Gln Gln Lys Pro Gly Gln
     50                  55                  60

Pro Pro Lys Leu Leu Ile Tyr Arg Ala Ser Thr Leu Ala Ser Gly Val
 65                  70                  75                  80

Pro Ser Arg Phe Lys Gly Ser Gly Ser Gly Thr Gln Phe Thr Leu Thr
                 85                  90                  95

Ile Ser Asp Leu Glu Cys Ala Asp Ala Ala Thr Tyr Tyr Cys Gln Gln
            100                 105                 110

Gly Phe Val Ile Ser Asn Val Leu Asn Ser Phe Gly Gly Gly Thr Glu
                115                 120                 125

Val Val Val Lys Gly Asp Pro Val Ala Pro Thr Val Leu Ile Phe Pro
130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
                180                 185                 190

Ala Asp Cys Thr Tyr Asn Leu Ser Ser Thr Leu Thr Leu Thr Ser Thr
            195                 200                 205

Gln Tyr Asn Ser His Lys Glu Tyr Thr Cys Lys Val Thr Gln Gly Thr
        210                 215                 220

Thr Ser Val Val Gln Ser Phe Asn Arg Gly Asp Cys
225                 230                 235

<210> SEQ ID NO 25
<211> LENGTH: 6
<212> TYPE: PRT
<213> ORGANISM: Artificial Sequence
<220> FEATURE:
<223> OTHER INFORMATION: Predicted CDR1 of VL sequence of monoclonal
      antibody Mab#42

<400> SEQUENCE: 25

Gln Ser Ile Tyr Ser Tyr
1               5

<210> SEQ ID NO 26
<211> LENGTH: 3
<212> TYPE: PRT
<213> ORGANISM: Artificial Sequence
<220> FEATURE:
<223> OTHER INFORMATION: Predicted CDR2 of VL sequence of monoclonal
      antibody Mab#42

<400> SEQUENCE: 26

Arg Ala Ser
1

<210> SEQ ID NO 27
<211> LENGTH: 12
<212> TYPE: PRT
<213> ORGANISM: Artificial Sequence
<220> FEATURE:
<223> OTHER INFORMATION: Predicted CDR3 of VL sequence of monoclonal
      antibody Mab#42

<400> SEQUENCE: 27

Gln Gln Gly Phe Val Ile Ser Asn Val Leu Asn Ser
1               5                   10
```

```
<210> SEQ ID NO 28
<211> LENGTH: 127
<212> TYPE: PRT
<213> ORGANISM: Artificial Sequence
<220> FEATURE:
<223> OTHER INFORMATION: Portion of VH sequence of an antibody that
      specifically binds an ERFE polypeptide
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (48)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (70)..(71)
<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: MISC_FEATURE
<222> LOCATION: (92)..(92)
<223> OTHER INFORMATION: Wherein Xaa may be present or absent, and if
      present Xaa is any amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (115)..(116)
<223> OTHER INFORMATION: Xaa can be any naturally occurring amino acid
<220> FEATURE:
<221> NAME/KEY: MISC_FEATURE
<222> LOCATION: (117)..(120)
<223> OTHER INFORMATION: Wherein each Xaa is independently present or
      absent, and if present Xaa is any amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (124)..(125)
<223> OTHER INFORMATION: Xaa can be any naturally occurring amino acid
<220> FEATURE:
<221> NAME/KEY: misc_feature
```

```
<222> LOCATION: (127)..(127)
<223> OTHER INFORMATION: Xaa can be any naturally occurring amino acid

<400> SEQUENCE: 28

Met Glu Thr Gly Leu Arg Trp Leu Leu Leu Val Ala Val Leu Lys Gly
1               5                   10                  15

Xaa Gln Cys Gln Ser Xaa Glu Glu Ser Gly Gly Arg Leu Val Thr Pro
            20                  25                  30

Gly Xaa Xaa Leu Thr Leu Thr Cys Thr Val Ser Gly Ile Asp Leu Xaa
        35                  40                  45

Xaa Xaa Xaa Met Xaa Trp Val Arg Gln Ala Pro Gly Lys Gly Leu Glu
50                  55                  60

Trp Ile Gly Val Ile Xaa Xaa Asp Xaa Xaa Xaa Xaa Tyr Ala Xaa Trp
65                  70                  75                  80

Xaa Lys Gly Arg Phe Thr Ile Ser Lys Thr Ser Xaa Thr Val Asp
            85                  90                  95

Leu Lys Xaa Thr Ser Xaa Thr Thr Glu Asp Thr Ala Thr Tyr Phe Cys
            100                 105                 110

Xaa Arg Xaa Xaa Xaa Xaa Xaa Xaa Tyr Arg Xaa Xaa Asp Xaa
            115                 120                 125

<210> SEQ ID NO 29
<211> LENGTH: 123
<212> TYPE: PRT
<213> ORGANISM: Artificial Sequence
<220> FEATURE:
<223> OTHER INFORMATION: Portion of VH sequence of monoclonal antibody
      Mab#9

<400> SEQUENCE: 29

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Asn
        35                  40                  45

Asp Asn Ala Met Arg Trp Val Arg Gln Ala Pro Gly Lys Gly Leu Glu
50                  55                  60

Trp Ile Gly Val Ile Tyr Ile Asp Thr Ser Thr Tyr Tyr Ala Ser Trp
65                  70                  75                  80

Ala Lys Gly Arg Phe Thr Ile Ser Lys Thr Ser Ser Thr Thr Val Asp
            85                  90                  95

Leu Lys Ile Thr Ser Pro Thr Thr Glu Asp Thr Ala Thr Tyr Phe Cys
            100                 105                 110

Val Arg Glu Asp Gly Tyr Arg Leu Gly Asp Val
            115                 120

<210> SEQ ID NO 30
<211> LENGTH: 126
<212> TYPE: PRT
<213> ORGANISM: Artificial Sequence
<220> FEATURE:
<223> OTHER INFORMATION: VH sequence of monoclonal antibody Mab#42

<400> SEQUENCE: 30

Met Glu Thr Gly Leu Arg Trp Leu Leu Leu Val Ala Val Leu Lys Gly
1               5                   10                  15

Ala Gln Cys Gln Ser Leu Glu Glu Ser Gly Gly Arg Leu Val Thr Pro
            20                  25                  30
```

```
Gly Gly Ser Leu Thr Leu Thr Cys Thr Val Ser Gly Ile Asp Leu Ser
        35                  40                  45

Ser Tyr Glu Met Gly Trp Val Arg Gln Ala Pro Gly Lys Gly Leu Glu
    50                  55                  60

Trp Ile Gly Val Ile Gly Thr Asp Gly Thr Ala Val Tyr Ala Thr Trp
65                  70                  75                  80

Val Lys Gly Arg Phe Thr Ile Ser Lys Thr Ser Thr Val Asp Leu
                85                  90                  95

Lys Met Thr Ser Leu Thr Thr Glu Asp Thr Ala Thr Tyr Phe Cys Ala
            100                 105                 110

Arg Asp Ser Ser Gly Asn Ser Asn Tyr Arg Ala Phe Asp Pro
            115                 120                 125

<210> SEQ ID NO 31
<211> LENGTH: 124
<212> TYPE: PRT
<213> ORGANISM: Artificial Sequence
<220> FEATURE:
<223> OTHER INFORMATION: Portion of VL sequence of an antibody that
      specifically binds an ERFE polypeptide
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(36)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: MISC_FEATURE
<222> LOCATION: (54)..(55)
<223> OTHER INFORMATION: Wherein each Xaa is indpendently present or
      absent, and if present Xaa is any amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (101)..(103)
<223> OTHER INFORMATION: Xaa can be any naturally occurring amino acid
<220> FEATURE:
<221> NAME/KEY: misc_feature
<222> LOCATION: (105)..(105)
```

<223> OTHER INFORMATION: Xaa can be any naturally occurring amino acid
<220> FEATURE:
<221> NAME/KEY: misc_feature
<222> LOCATION: (113)..(118)
<223> OTHER INFORMATION: Xaa can be any naturally occurring amino acid
<220> FEATURE:
<221> NAME/KEY: misc_feature
<222> LOCATION: (121)..(124)
<223> OTHER INFORMATION: Xaa can be any naturally occurring amino acid

<400> SEQUENCE: 31

```
Met Asp Thr Arg Ala Pro Thr Gln Leu Leu Gly Leu Leu Leu Leu Trp
1               5                   10                  15

Leu Pro Xaa Ala Arg Cys Ala Xaa Xaa Met Thr Gln Thr Pro Xaa Ser
            20                  25                  30

Val Xaa Xaa Xaa Val Gly Gly Thr Val Thr Ile Xaa Cys Gln Ala Ser
        35                  40                  45

Gln Ser Xaa Tyr Xaa Xaa Xaa Tyr Leu Ser Trp Xaa Gln Gln Lys Pro
    50                  55                  60

Gly Gln Pro Pro Lys Leu Leu Ile Tyr Xaa Ala Ser Thr Leu Ala Ser
65                  70                  75                  80

Gly Val Pro Ser Arg Phe Xaa Gly Ser Gly Ser Gly Thr Gln Phe Thr
                85                  90                  95

Leu Thr Ile Ser Xaa Xaa Xaa Cys Xaa Asp Ala Ala Thr Tyr Tyr Cys
                100                 105                 110

Xaa Xaa Xaa Xaa Xaa Xaa Ser Asn Xaa Xaa Xaa Xaa
            115                 120
```

<210> SEQ ID NO 32
<211> LENGTH: 124
<212> TYPE: PRT
<213> ORGANISM: Artificial Sequence
<220> FEATURE:
<223> OTHER INFORMATION: Portion of VL sequence of monoclonal antibody Mab#9

<400> SEQUENCE: 32

```
Met Asp Thr Arg Ala Pro Thr Gln Leu Leu Gly Leu Leu Leu Leu Trp
1               5                   10                  15

Leu Pro Asp Ala Arg Cys Ala Leu Val Met Thr Gln Thr Pro Ser Ser
            20                  25                  30

Val Ser Ala Gly Val Gly Gly Thr Val Thr Ile Asn Cys Gln Ala Ser
        35                  40                  45

Gln Ser Leu Tyr Asn Asn Asn Tyr Leu Ser Trp Phe Gln Gln Lys Pro
    50                  55                  60

Gly Gln Pro Pro Lys Leu Leu Ile Tyr Trp Ala Ser Thr Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Gly Val Ala Cys Asp Asp Ala Ala Thr Tyr Tyr Cys
                100                 105                 110

Ala Gly Tyr Lys Ser Ser Ser Asn Asp Asp Phe Ala
            115                 120
```

<210> SEQ ID NO 33
<211> LENGTH: 122
<212> TYPE: PRT
<213> ORGANISM: Artificial Sequence
<220> FEATURE:
<223> OTHER INFORMATION: Portion of VL sequence of monoclonal antibody Mab#42

```
<400> SEQUENCE: 33

Met Asp Thr Arg Ala Pro Thr Gln Leu Leu Gly Leu Leu Leu Trp
1               5                   10                  15

Leu Pro Gly Ala Arg Cys Ala Tyr Asp Met Thr Gln Thr Pro Ala Ser
                20                  25                  30

Val Glu Val Ala Val Gly Gly Thr Val Thr Ile Lys Cys Gln Ala Ser
            35                  40                  45

Gln Ser Ile Tyr Ser Tyr Leu Ser Trp Tyr Gln Gln Lys Pro Gly Gln
    50                  55                  60

Pro Pro Lys Leu Leu Ile Tyr Arg Ala Ser Thr Leu Ala Ser Gly Val
65                  70                  75                  80

Pro Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Gln
                100                 105                 110

Gly Phe Val Ile Ser Asn Val Leu Asn Ser
            115                 120

<210> SEQ ID NO 34
<211> LENGTH: 15
<212> TYPE: PRT
<213> ORGANISM: Artificial Sequence
<220> FEATURE:
<223> OTHER INFORMATION: Portion of antigenic linear epitope of
      recombinant human erythroferrone

<400> SEQUENCE: 34

Leu Gly Ser Pro Glu Pro Gly Ala Pro Ser Arg Ser Arg Ala Arg
1               5                   10                  15
```

IMMUNOASSAY FOR HUMAN ERYTHROFERRONE

CROSS-REFERENCE TO RELATED APPLICATIONS

This application claims the benefit of U.S. patent application Ser. No. 62/515,679, filed Jun. 6, 2017, which is herein incorporated by reference in its entirety.

ACKNOWLEDGEMENT OF GOVERNMENT SUPPORT

This invention was made with Government support under DK065029 and HL119893, awarded by the National Institutes of Health. The Government has certain rights in the invention.

REFERENCE TO A SEQUENCE LISTING SUBMITTED VIA EFS-WEB

The content of the ASCII text file of the sequence listing named "20180523_034044_175WO1_seq_ST25" which is 53.6 kb in size was created on May 23, 2018 and electronically submitted via EFS-Web herewith the application is incorporated herein by reference in its entirety.

BACKGROUND OF THE INVENTION

1. FIELD OF THE INVENTION

The present invention relates to assays for erythroferrone.

2. DESCRIPTION OF THE RELATED ART

Intestinal iron absorption and the release of iron from stores increase greatly within hours after blood loss or administration of erythropoietin. In murine models, the response is largely mediated by erythroferrone. Erythroferrone is a glycoprotein hormone secreted by erythropoietin-stimulated erythroblasts. Erythroferrone is made in the marrow of a subject and its production is greatly increased when the production of red blood cells is stimulated, e.g., after bleeding or during recovery from anemia. Erythroferrone acts by suppressing the hepatic synthesis of the master iron-regulatory hormone, hepcidin. Pathologically increased erythroferrone contributes to hepcidin suppression and iron overload in a mouse model of non-transfused β-thalassemia.

SUMMARY OF THE INVENTION

In some embodiments, the present invention provides a method of making an antibody against human erythroferrone and/or an ERFE polypeptide, which comprises injecting a non-human animal with human erythroferrone, ELPRGPGESRAGPAARPP (SEQ ID NO: 1), GESRAG (SEQ ID NO: 2), LGSPEPGAPSRSRAR (SEQ ID NO: 34), rhERFE1 (SEQ ID NO: 3), and/or rhERFE2 (SEQ ID NO: 7), preferably rhERFE1 (SEQ ID NO: 3) or rhERFE2 (SEQ ID NO: 7), and more preferably rhERFE2 (SEQ ID NO: 7).

In some embodiments, the present invention provides an antibody produced by a method as described herein, e.g., paragraphX [0013]. In some embodiments, the present invention provides an antibody that comprises GIDLNDNA (SEQ ID NO: 10), IYIDTST (SEQ ID NO: 11), VREDGYRLGDV (SEQ ID NO: 12), QSLYNNNY (SEQ ID NO: 15), WAS (SEQ ID NO: 16), and AGYKSSSNDDFA (SEQ ID NO: 17). In some embodiments, the present invention provides an antibody that comprises GIDLSSYE (SEQ ID NO: 20), IGTDGTA (SEQ ID NO: 21), ARDSSGNSNYRAFDP (SEQ ID NO: 22), QSIYSY (SEQ ID NO: 25), RAS (SEQ ID NO: 26), and QQGFVISNVLNS (SEQ ID NO: 27). In some embodiments, the present invention provides an antibody comprising a VH sequence as described herein, e.g., paragraph [0096]. In some embodiments, the present invention provides an antibody comprising VL sequence as described herein, e.g., paragraph [0097]. In some embodiments, the antibody comprises a VH sequence as described in paragraph [0097] and a VL sequence as described in paragraph [0097]. In some embodiments, the present invention provides an antibody or an immunologically active portion thereof comprising a VH sequence as described in paragraph [0096] and/or a VL sequence as described in paragraph [0097]. In some embodiments, the antibody or the immunologically active portion specifically binds human erythroferrone or an analog thereof, ELPRGPGESRAGPAARPP (SEQ ID NO: 1), GESRAG (SEQ ID NO: 2), LGSPEPGAPSRSRAR (SEQ ID NO: 34), rhERFE1 (SEQ ID NO: 3), and/or rhERFE2 (SEQ ID NO: 7). In some embodiments, the antibody is a monoclonal antibody or a synthetic antibody. In some embodiments, the antibody is an IgG isotype.

In some embodiments, the present invention provides an immunoassay for detecting an ERFE polypeptide, such as a human erythroferrone or an analog thereof, in a sample, which comprises a1) contacting the sample with a capture reagent that specifically binds the ERFE polypeptide and then contacting with at least one detection reagent that specifically binds the ERFE polypeptide bound to the capture reagent, or a2) contacting the sample with at least one detection reagent that specifically binds the ERFE polypeptide and then contacting with a capture reagent that specifically binds the ERFE polypeptide bound to the at least one detection reagent; and b) detecting or measuring a detectable label of the at least one detection reagent bound to the ERFE polypeptide that is bound to the capture reagent. In some embodiments, the capture reagent and/or the at least one detection reagent is an antibody as described herein, e.g., paragraph [0014], which if both the capture reagent and/or the at least one detection reagent are antibodies, the antibodies may be the same or different. In some embodiments, the capture reagent or the at least one detection reagent is an antibody that specifically binds a three-dimensional epitope of the ERFE polypeptide. In some embodiments, the capture reagent or the at least one detection reagent is an antibody that specifically binds a linear epitope of the ERFE polypeptide. In some embodiments, the capture reagent is an antibody that specifically binds a linear epitope of the ERFE polypeptide and the at least one detection reagent is an antibody specifically binds a three-dimensional epitope of the ERFE polypeptide. In some embodiments, the linear epitope comprises or consists of the amino acid sequence ELPRGPGESRAGPAARPP (SEQ ID NO: 1). In some embodiments, the linear epitope comprises or consists of the amino acid sequence GESRAG (SEQ ID NO: 2). In some embodiments, the linear epitope comprises or consists of the amino acid sequence LGSPEPGAPSRSRAR (SEQ ID NO: 34). In some embodiments, the antibody was raised against rhERFE1 (SEQ ID NO: 3) or rhERFE2 (SEQ ID NO: 7). In some embodiments, the immunoassay further comprises immobilizing the capture reagent to an assay substrate. In some embodiments, the sample is obtained from a human subject. In some embodiments, the blood sample is a whole blood sample, a serum sample, or a plasma sample.

In some embodiments, the present invention provides a method of determining whether the level of erythroferrone in a subject is low or high as compared to a control, which comprises performing the immunoassay as described herein, e.g., paragraph [0015] on a sample obtained from the subject to obtain a measured level of erythroferrone, and comparing the measured level of erythroferrone to a control. In some embodiments, the method further comprises characterizing the subject as having an abnormally high level of erythroferrone where the measured level of erythroferrone is more than 30 ng/ml. In some embodiments, the method further comprises diagnosing the subject as having an iron metabolism disease, wherein the measured level of erythroferrone is abnormally low or abnormally high. In some embodiments, the subject is diagnosed as having a disease or condition related to abnormally low levels of erythroferrone where the measured level of erythroferrone is abnormally low or the subject is diagnosed as having a disease or condition related to abnormally high levels of erythroferrone where the measured level of erythroferrone is abnormally high. In some embodiments, the subject is human.

In some embodiments, the present invention provides a method of treating a subject for an iron metabolism disease, which comprises administering to the subject a erythroferrone therapeutic when the subject has been characterized has having an abnormally high level of erythroferrone using an immunoassay as described herein, e.g., paragraph [0015], such as the method described at paragraph [0016]. In some embodiments, the erythroferrone therapeutic is a compound that modulates iron uptake, preferably hepcidin, a mini-hepcidins, or a modified mini-hepcidin. In some embodiments, the subject is human.

In some embodiments, the present invention provides a kit comprising one or more antibodies as described herein, e.g., paragraph [0014], packaged together with one or more components, e.g., detection reagents, buffers, blocking agents, assay substrates, etc., to, for example, assay an ERFE polypeptide such as human erythroferrone or an analog thereof. In some embodiments, the present invention provides a kit comprising one or more ERFE polypeptides, e.g., ELPRGPGESRAGPAARPP (SEQ ID NO: 1), GESRAG (SEQ ID NO: 2), LGSPEPGAPSRSRAR (SEQ ID NO: 34), rhERFE1 (SEQ ID NO: 3), and/or rhERFE2 (SEQ ID NO: 7), packaged together with one or more components, e.g., detection reagents, buffers, blocking agents, assay substrates, to, for example, capture or assay antibodies against an ERFE polypeptide such as human erythroferrone or an analog thereof.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description explain the principles of the invention.

DESCRIPTION OF THE DRAWINGS

This invention is further understood by reference to the drawings wherein.

DETAILED DESCRIPTION OF THE INVENTION

Figure 1:
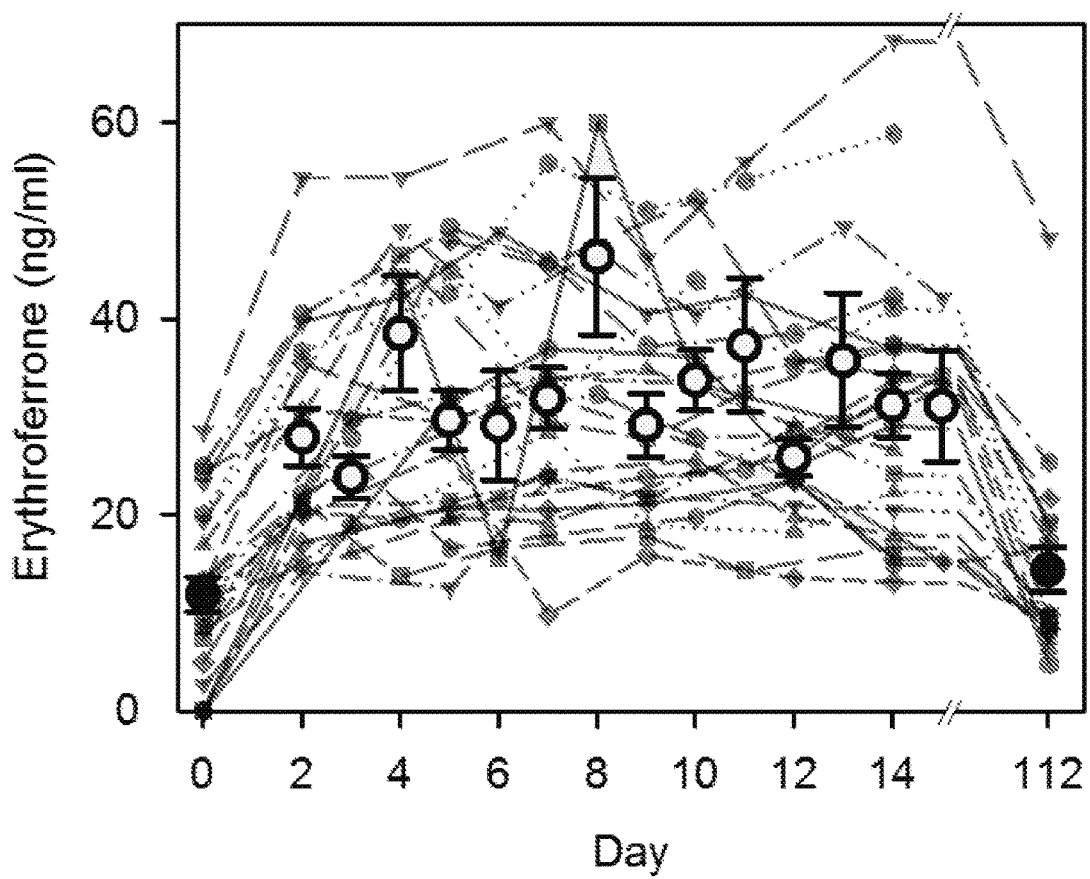
FIG. 1: Serum erythroferrone in blood donors of 2 u of erythrocytes. Lines denote individual donors. Circles and error bars show mean±SEM for each time point. Red denotes $p<0.05$ by One Way ANOVA compared to initial baseline (day 0) concentration. The first post-donation sample was obtained at average 2.5 days after donation (range 2-4 days), and showed an increase in all samples, by 16.4±8.9 ng/ml over initial sample (mean increase±SD, $p=0.0002$, paired t-test, n=24). Further rise of serum hERFE was seen in most donors with a maximum at 8±4 days (mean±SD, n=24) increasing by 26.7±11.2 ng/ml over initial value. By 120 days after the blood donation, serum hERFE concentrations returned to baseline (3.9±7.5 ng/ml over initial, $p=0.28$ comparing baseline and 112 days, paired t-test, n=20).

Disclosed herein is an assay for an erythroferrone, such as human erythroferrone (hERFE) or an analog thereof. The experiments herein show that the assay detects the analogous physiological hERFE increases in humans subjected to blood loss or erythropoietin administration, as well as the pathological increases of hERFE in subjects suffering from β-thalassemia.

The assay exemplified herein is the first validated immunoassay for hERFE. Applications of the assays according to the present invention include diagnosing anemia (e.g., diagnosing ineffective erythropoiesis), assessing therapeutic responses to erythropoietin agonists, detecting doping with erythropoietin or erythropoietin agonists (including synthetic analogs that result in elevated serum erythroferrone), diagnosing iron metabolism diseases involving abnormal hERFE levels, and providing differential diagnoses of polycythemia.

As used herein, "iron metabolism diseases" refers to diseases where aberrant iron metabolism directly causes the disease, diseases caused by iron blood levels that are dysregulated, and diseases that can be treated by modulating iron levels, and include iron overload diseases, iron deficiency disorders, disorders of iron biodistribution, and disorders of iron metabolism, etc. Examples of iron metabolism diseases include hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia intermedia, alpha thalassemia, sideroblastic anemia, porphyria, porphyria cutanea tarda, African iron overload, hyperferritinemia, ceruloplasmin deficiency, atransferrinemia, congenital dyserythropoietic anemia, anemia of chronic disease, anemia of inflammation, anemia of infection, hypochromic microcytic anemia, iron-deficiency anemia, iron-refractory iron deficiency anemia, anemia of chronic kidney disease, erythropoietin resistance, iron deficiency of obesity, other anemias, benign or malignant tumors that overproduce hepcidin or induce its overproduction, conditions with hepcidin excess, Friedreich ataxia, gracile syndrome, Hallervorden-Spatz disease, Wilson's disease, pulmonary hemosiderosis, hepatocellular carcinoma, cancer, hepatitis, cirrhosis of liver, pica, chronic renal failure, insulin resistance, diabetes, atherosclerosis, neurodegenerative disorders, multiple sclerosis, Parkinson's disease, Huntington's disease, and Alzheimer's disease. In some embodiments, the iron overload disease is myelodysplastic syndrome. In some embodiments, iron metabolism diseases are not typically identified as being iron related. For example, diabetes (Type I or Type II), insulin resistance, glucose intolerance, and other disorders may be ameliorated by treating underlying iron metabolism disorders. See Simcox, et al. (2013) Cell Metab. Mar. 5; 17(3): 329-341, which is herein incorporated by reference. As such, these diseases are encompassed under the broad definition. Those skilled in the art are readily able to determine whether a given disease is an iron metabolism disease using methods in the art, including the assays of WO 2004092405, and assays which monitor hepcidin, hemojuvelin, or iron levels and expression, such as those described in U.S. Pat. No. 7,534,764. In some embodiments, the iron metabolism disease is a disease or condition related to abnormally high levels of erythroferrone. In some embodiments, the iron metabolism disease is a disease or condition related to abnormally low levels of erythroferrone.

Generally, serum concentration levels of erythroferrone reflect the levels of erythropoietin (as erythropoietin stimulates secretion of erythroferrone) and/or the number of erythroblasts (which are the cells that secrete erythroferrone). Examples of a "disease or condition related to abnormally low levels of erythroferrone" include erythropoietin deficiencies, anemia of chronic disease (also called anemia of inflammation), anemias associated with acute or chronic infections, anemia of chronic kidney disease, pure red cell aplasia, aplastic anemia, radiation, and chemicals or poisons that cause aplastic anemia (e.g., pesticides, arsenic, benzene, chemotherapeutics, and chloramphenicol. Examples of a "disease or condition related to abnormally high levels of erythroferrone" include α-thalassemia, β-thalassemia, congenital dyserythropoietic anemias, ineffective erythropoiesis, chronic liver diseases including alcoholic liver disease and chronic hepatitis B and C, blood loss, acute hypoxia, polycythemia (e.g., due to activation of the erythropoietin receptor or its pathways (e.g., polycythemia vera), hemolytic anemias, treatment or doping with erythropoietin or an agonist thereof, intravenous water infusion (not half-normal saline or normal saline), exposure to chemicals or poisons that induce hemolysis (such as anti-malaria drugs (quinine compounds), arsenic, dapsone, metals (chromium/chromates, platinum salts, nickel compounds, copper, lead, cisplatinum), nitrites, nitrofurantoin, penicillin, phenazopyridine (Pyridium), rho immune globulin (WinRho), ribavirin, hemolytic toxins (e.g., snake venom), sulfonamides, sulfones, etc.), and exposure to chemicals or poisons that mimic hypoxia and/or induce erythropoietin and erythroferrone (e.g., cobalt).

Properties of the Erythroferrone Assay

The standard curve was linear after log-log transformation. Limit of blanks (64 replicates), calculated as average+ 1.645*standard deviation of blanks, was 0.8 ng/ml. The limit of detection, calculated as average+1.645*standard deviation of the concentration calculated from 64 replicates of the lowest standard (0.625 ng/ml) was 1.5 ng/ml. The lower limit of quantitation (LLQ) was determined as 14 ng/ml by analyzing at ten-fold sample dilution the CV % of 16 replicates each of 8 human samples with low hERFE concentrations, graphing CV % vs hERFE concentration, fitting the relationship with an exponential curve, and interpolating an hERFE concentration that yielded CV %=20. The working range was therefore 14-100 ng/ml. Spike recovery was determined by adding 2.5, 5.0, or 10 ng/ml of rhERFE2 to ten-fold dilutions of human serum samples (n=9) containing very low concentrations of hERFE (0 to 0.8 ng/ml), measuring for each sample the resulting hERFE concentration and subtracting its pre-spike hERFE concentration. The spike recovery (mean±SD) was 92±8%, 100±5% and 111±4% for spikes of 2.5, 5.0, or 10 ng/ml respectively, corresponding to sample concentrations of 25, 50 and 100 ng/ml.

hERFE Response to Erythropoietic Stimulation hERFE concentration in male, female, and combined blood donors prior to donation (baseline) was 12±9 ng/ml (mean±SD, n=28), 11±11 ng/ml (n=30) and 12±10 ng/ml (n=58). The distributions were skewed so that median and percentile range (25%, 75%) was 12 (7, 19), 7 (4, 9) and 8 (4, 15) for men, women, and combined genders. Follow-up on the male donors for up to 112 days (FIG. 1) showed that serum hERFE rose in the second sample in all donors (on average 2.5 days after donation, range 2-4 days) to 28±11 ng/ml ($p=3\times10^{-7}$, paired t-test compared to baseline). Further rise of serum hERFE was seen in most donors with a maximum reaching 38±13 ng/ml (n=29, $p=5\times10^{-11}$) at 9±4 days. At 112 days following donation, serum hERFE concentrations returned to baseline (15±10 ng/ml, p=0.3, n=23). Mean serum hepcidin was suppressed on days 2-15 but returned towards baseline by 112 days (manuscript in preparation).

Figure 2:
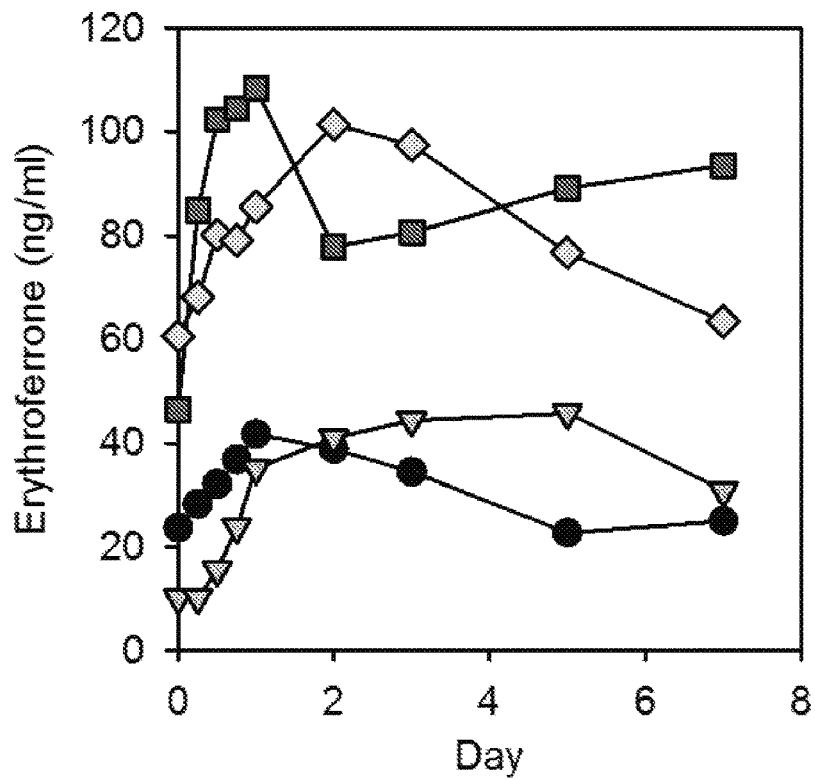
FIG. 2: Serum erythroferrone in four patients with moderate anemia treated on day 0 with erythropoietin 20,000 units SC. Blood samples were obtained every 6 hours the first day, then on mornings of days 2, 3, 5, and 7.
Figure 3:
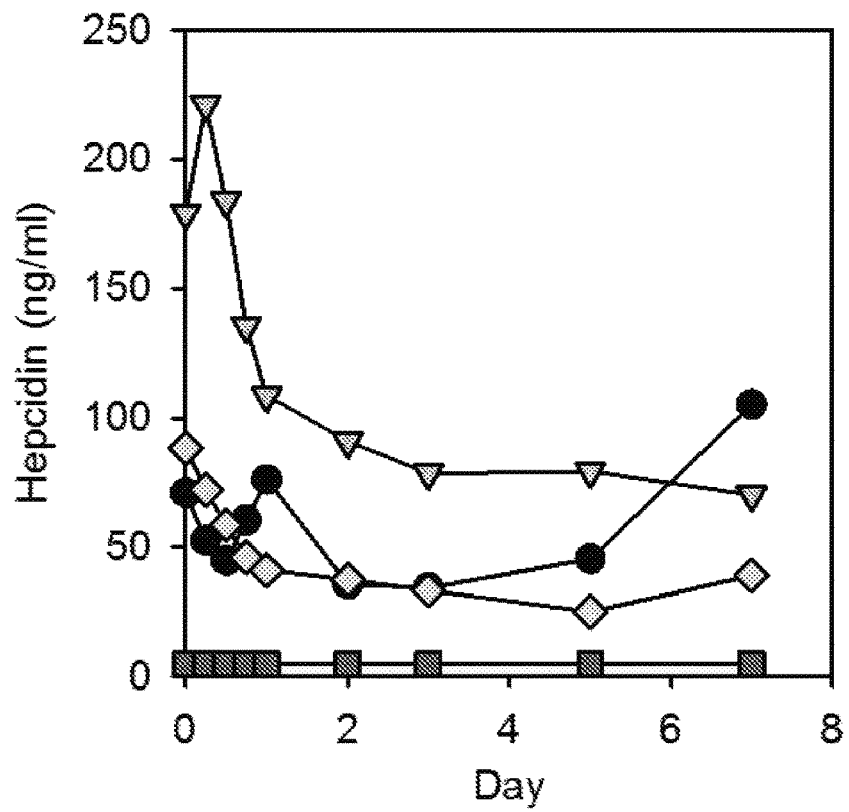
FIG. 3: Serum hepcidin in the same samples as FIG. 2. The patient designated by green symbols was iron-deficient (serum ferritin 14, transferrin saturation 17%, undetectable serum hepcidin).

Responses to the administration of erythropoietin 20,000 units in four geriatric patients with moderate anemia of unknown etiology was also examined (FIG. 2 and FIG. 3). hERFE increased in all patients, reaching a maximum at 1-5 days, coincident with a decline in serum hepcidin concentrations.

Figure 4:
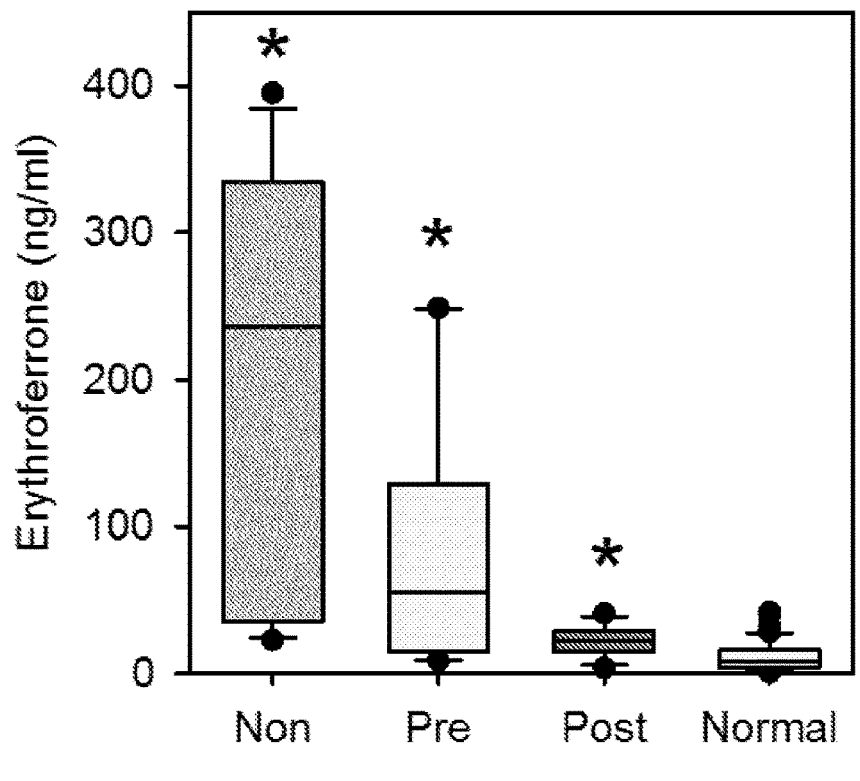
FIG. 4: Serum hERFE in patients with β-thalassemia, non-transfused (Non), before transfusion (Pre) or after transfusion (Post). Box plots show median, box 25% to 75%, whiskers 10% to 90%, and outliers. Serum hERFE levels were massively increased in thalassemic patients, non-transfused and pre-transfusion but were closer to normal after transfusion, *$p<0.05$, One Way ANOVA on Ranks, comparing to normal reference group.
Figure 5:
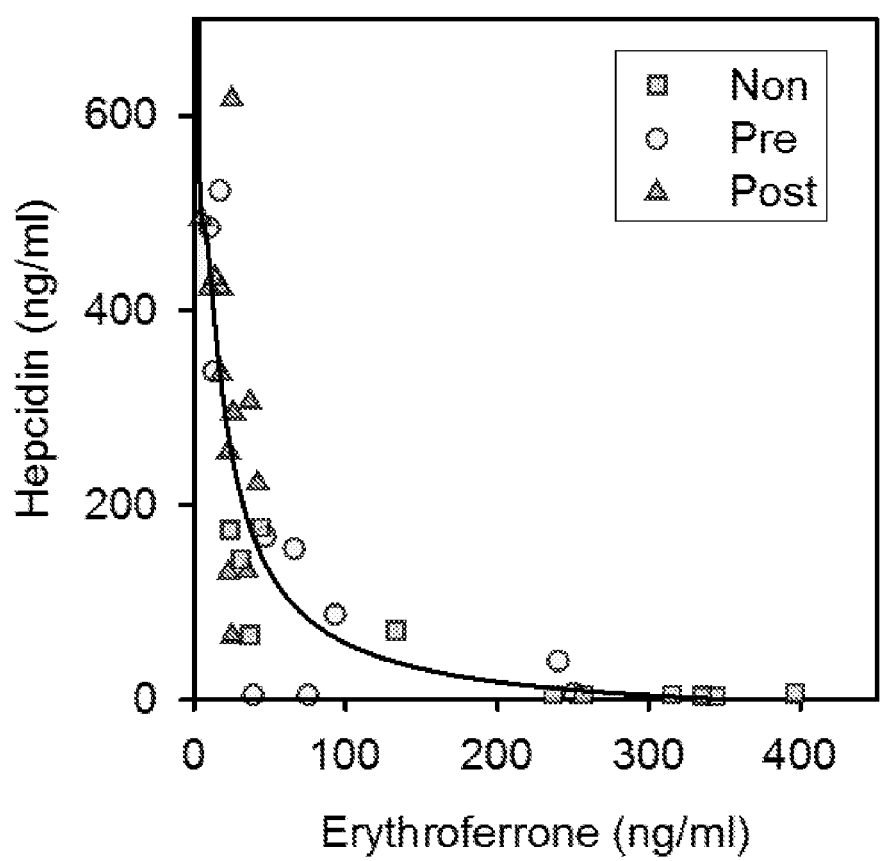
FIG. 5: Serum hepcidin in the same samples, vs erythroferrone, scatterplot is fitted by an inverse third order equation, $R^2=0.7$.

Pathological Increase of hERFE in β-thalassemia hERFE concentrations in non-transfused and pre-transfusion patients were greatly increased compared to the reference sample from blood donors at baseline (FIG. 4, p<0.05, One-way ANOVA on ranks, Dunn's Method). Hepcidin concentrations inversely correlated with erythroferrone concentrations (FIG. 5), consistent with the proposed role of hERFE as a pathological hepcidin suppressor in β-thalassemia.

Antibodies against hERFE and ERFE Polypeptides

In some embodiments, the present invention provides antibodies against one or more ERFE polypeptides, preferably hERFE. As used herein, "ERFE polypeptides" refers to an erythroferrone (preferably hERFE), analogs of hERFE, homologs of hERFE, and fragments thereof. In some embodiments, the ERFE polypeptide is a protein that comprises or consists of comprises or consists of ELPRGPGESRAGPAARPP (SEQ ID NO: 1), GESRAG (SEQ ID NO: 2), or LGSPEPGAPSRSRAR (SEQ ID NO: 34). In some embodiments, the ERFE polypeptide is an erythroferrone from an *Aotus* spp., a *Cercocebus* spp., an *Equus* spp., a *Gorilla* spp., *Homo sapiens*, a *Macaca* spp., a *Microcebus* spp., a *Neomonachus* spp., a *Nomascus* spp., an *Odobenus* spp., a *Pan* spp., a *Papio* spp., a *Piliocolobus* spp., a *Pongo* spp., a *Rhinolophus* spp., or a *Rhinopithecus* spp. In some embodiments, the ERFE polypeptide is an erythroferrone from one of the following species: *Aotus nancymaae, Cercocebus atys, Equus caballus, Gorilla gorilla gorilla, Homo sapiens, Macaca fascicularis, Macaca mulatta, Macaca nemestrina, Microcebus murinus, Neomonachus schauinslandi, Nomascus leucogenys, Odobenus rosmarus divergens, Pan troglodytes, Papio anubis, Piliocolobus tephrosceles, Pongo abelii, Rhinolophus sinicus*, and *Rhinopithecus roxellana*. In some embodiments, the ERFE polypeptide is a human erythroferrone. In some embodiments, the ERFE polypeptide is an analog of human erythroferrone. In some embodiments, the ERFE polypeptide is a macaque erythroferrone.

As used herein, "analogs" refer to proteins (or nucleic acid molecules) of heterologous origins that display the same or substantially similar activity. As used herein, "homologs" refer to proteins (or nucleic acid molecules) of a common origin, but do not necessarily exhibit the same or substantially similar activity. Thus, ERFE polypeptides may or may not exhibit erythroferrone activity. As used herein, "erythroferrone activity" refers to the ability of the given substance to decrease hepatic hepcidin mRNA or serum hepcidin levels as compared to a negative control. As used herein, the terms "protein", "polypeptide" and "peptide" are used interchangeably to refer to two or more amino acids linked together. Groups or strings of amino acid abbreviations are used to represent peptides. Except when specifically indicated, peptides are indicated with the N-terminus on the left and the sequence is written from the N-terminus to the C-terminus.

As used herein, a given percentage of "sequence identity" refers to the percentage of nucleotides or amino acid residues that are the same between sequences, when compared and optimally aligned for maximum correspondence over a given comparison window, as measured by visual inspection or by a sequence comparison algorithm in the art, such as the BLAST algorithm, which is described in Altschul et al., J. Mol. Biol. 215:403-410 (1990). Software for performing BLAST (e.g., BLASTP and BLASTN) analyses is publicly available through the National Center for Biotechnology Information (ncbi.nlm.nih.gov). The comparison window can exist over a given portion, e.g., a functional domain, or an arbitrarily selection a given number of contiguous nucleotides or amino acid residues of one or both sequences. Alternatively, the comparison window can exist over the full length of the sequences being compared. For purposes herein, where a given comparison window (e.g., over 80% of the given sequence) is not provided, the recited sequence identity is over 100% of the given sequence. Additionally, for the percentages of sequence identity of the proteins provided herein, the percentages are determined using BLASTP 2.8.0+, scoring matrix BLOSUM62, and the default parameters available at blast.ncbi.nlm.nih.gov/Blast.cgi. See also Altschul, et al. (1997), Nucleic Acids Res. 25:3389-3402; and Altschul, et al. (2005) FEBS J. 272: 5101-5109.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

ERFE polypeptides of the present invention may be made using methods known in the art including chemical synthesis, biosynthesis or in vitro synthesis using recombinant DNA methods, and solid phase synthesis. See e.g., Kelly & Winkler (1990) Genetic Engineering Principles and Methods, vol. 12, J. K. Setlow ed., Plenum Press, NY, pp. 1-19; Merrifield (1964) J Amer Chem Soc 85:2149; Houghten (1985) PNAS USA 82:5131-5135; and Stewart & Young (1984) Solid Phase Peptide Synthesis, 2ed. Pierce, Rockford, Ill., which are herein incorporated by reference. ERFE polypeptides of the present invention may be purified using protein purification techniques known in the art such as reverse phase high-performance liquid chromatography (HPLC), ion-exchange or immunoaffinity chromatography, filtration or size exclusion, or electrophoresis. See Olsnes and Pihl (1973) Biochem. 12(16):3121-3126; and Scopes (1982) Protein Purification, Springer-Verlag, NY, which are herein incorporated by reference. Alternatively, polypeptides of the present invention may be made by recombinant DNA techniques known in the art.

As used herein, "antibody" refers to naturally occurring and synthetic immunoglobulin molecules and immunologically active portions thereof (i.e., molecules that contain an antigen binding site that specifically bind the molecule to which antibody is directed against). As such, the term antibody encompasses not only whole antibody molecules, but also antibody multimers and antibody fragments as well as variants (including derivatives) of antibodies, antibody multimers and antibody fragments. Examples of molecules which are described by the term "antibody" herein include: single chain Fvs (scFvs), Fab fragments, Fab' fragments, F(ab')2, disulfide linked Fvs (sdFvs), Fvs, and fragments comprising or alternatively consisting of, either a VL or a VH domain.

In some embodiments, antibodies of the present invention specifically bind one or more ERFE polypeptides. In some embodiments, the antibodies specifically bind an erythroferrone or a fragment thereof. In some embodiments, the antibodies specifically bind hERFE or a fragment thereof. In some embodiments, the antibodies are raised against rhERFE1 or rhERFE2. In some embodiments, the antibodies are monoclonal antibodies. In some embodiments, the monoclonal antibodies are obtained from rabbit-based hybridomas. As used herein, a compound (e.g., receptor or antibody) "specifically binds" a given target (e.g., ligand or epitope) if it reacts or associates more frequently, more rapidly, with greater duration, and/or with greater binding affinity with the given target than it does with a given alternative, and/or indiscriminate binding that gives rise to non-specific binding and/or background binding. As used herein, "non-specific binding" and "background binding" refer to an interaction that is not dependent on the presence of a specific structure (e.g., a given epitope). An example of an antibody that specifically binds an erythroferrone is an antibody that binds the erythroferrone with greater affinity, avidity, more readily, and/or with greater duration than it does to other compounds. An antibody that specifically binds an erythroferrone over a specified alternative is an antibody that binds the erythroferrone with greater affinity, avidity, more readily, and/or with greater duration than it does to the specified alternative. An antibody that specifically binds a given epitope of an erythroferrone is an antibody that binds the given epitope with greater affinity, avidity, more readily, and/or with greater duration than it does to other epitopes of the erythroferrone. As used herein, an "epitope" is the part of a molecule that is recognized by an antibody. Epitopes may be linear epitopes or three-dimensional epitopes. As used herein, the terms "linear epitope" and "sequential epitope" are used interchangeably to refer to a primary structure of an antigen, e.g., a linear sequence of consecutive amino acid residues, that is recognized by an antibody. As used herein, the terms "three-dimensional epitope" and "conformational epitope" are used interchangeably to refer a three-dimensional structure that is recognized by an antibody, e.g., a plurality of non-linear amino acid residues that together form an epitope when a protein is folded.

As used herein, "binding affinity" refers to the propensity of a compound to associate with (or alternatively dissociate from) a given target and may be expressed in terms of its dissociation constant, Kd. In some embodiments, an antibody according to the present invention has a Kd of $10^{-5}$ or less, $10^{-6}$ or less, preferably $10^{-7}$ or less, more preferably $10^{-8}$ or less, even more preferably $10^{-9}$ or less, and most preferably $10^{-10}$ or less to its given target. Binding affinity can be determined using methods in the art, such as equilibrium dialysis, equilibrium binding, gel filtration, immunoassays, surface plasmon resonance, and spectroscopy using experimental conditions that exemplify the conditions under which the compound and the given target may come into contact and/or interact. Dissociation constants may be used determine the binding affinity of a compound for a given target relative to a specified alternative. Alternatively, methods in the art, e.g., immunoassays, in vivo or in vitro assays for functional activity, etc., may be used to determine the binding affinity of the compound for the given target relative to the specified alternative. Thus, in some embodiments, the binding affinity of the antibody for the given target is at least 1-fold or more, preferably at least 5-fold or more, more preferably at least 10-fold or more, and most preferably at least 100-fold or more than its binding affinity for the specified alternative.

In some embodiments, the antibodies of the present invention are IgG isotype antibodies. In some embodiments, the antibodies of the present invention are monoclonal antibodies. In some embodiments, the monoclonal antibodies are obtained from rabbit-based monoclonal antibodies.

Immunoassays

In some embodiments, the present invention provides assays for detecting ERFE polypeptides. In some embodiments, the present invention provides assays for detecting analogs and/or homologs of human erythroferrone. In some embodiments, an analog of human erythroferrone is an erythroferrone from an *Aotus* spp., a *Cercocebus* spp., an *Equus* spp., a *Gorilla* spp., *Homo sapiens*, a *Macaca* spp., a *Microcebus* spp., a *Neomonachus* spp., a *Nomascus* spp., an *Odobenus* spp., a *Pan* spp., a *Papio* spp., a *Piliocolobus* spp., a *Pongo* spp., a *Rhinolophus* spp., or a *Rhinopithecus* spp. In some embodiments, the present invention provides assays for detecting full-length human erythroferrone. Assays according to the present invention include any immunoassay format in the art such as enzyme immune assays (EIAs), magnetic immunoassays (MIAs), counting immunoassays (CIAs), chemiluminescent immunoassays (CLIAs), radio-immunoassays (RIAs), electrochemiluminescence immunoassays (ECLIAs), fluorescent immunoassays (FIA), enzyme-linked immunosorbent assays (ELISAs), Western blot assays, and lateral flow tests (LFTs), and the like. The assays may be automated or manual. The various assays may employ any suitable labeling and detection system. The sensitivity and specificity of the assays according to the present invention can be further improved by optimizing the assay conditions, e.g., reaction times and temperatures, and/or modifying or substituting the reagents, e.g., different detection and labeling system, using methods in the art. In some embodiments, the immunoassay is an ELISA assay. In some embodiments, the immunoassay is a sandwich ELISA assay. In some embodiments, the immunoassay is a lateral flow test.

Generally, to perform an assay according to the present invention, a sample to be tested is obtained. As used herein, the term "sample" includes specimens and cultures obtained from any source, as well as biological samples and environmental samples. Biological samples may be obtained from animals (including humans) and encompass fluids, solids, tissues, and gases. Biological samples include blood products, such as plasma, serum, and the like. A biological sample can be obtained from a subject using methods in the art. A sample to be analyzed using one or more methods described herein can be either an initial unprocessed sample taken from a subject or a subsequently processed, e.g., partially purified, diluted, concentrated, fluidized, pretreated with a reagent (e.g., protease inhibitor, anti-coagulant, etc.), and the like. In some embodiments, the sample is a blood sample. In some embodiments, the blood sample is a whole blood sample, a serum sample, or a plasma sample. In some embodiments, the sample may be processed, e.g., condensed, diluted, partially purified, and the like. In some embodiments, the sample is pretreated with a reagent, e.g., a protease inhibitor. In some embodiments, two or more samples are collected at different time intervals to assess any difference in the amount of the analyte of interest, the progression of a disease or disorder, or the efficacy of a treatment. The test sample is then contacted with a capture reagent and, if the analyte is present, a conjugate between the analyte and the capture reagent is formed and is detected and/or measured with a detection reagent.

As used herein, a "capture reagent" refers to a molecule which specifically binds an analyte of interest. For example, if the analyte of interest is an antibody, the capture reagent may be an antigen or an epitope thereof to which the antibody specifically binds. As used herein, a "detection reagent" refers to a substance that has a detectable label attached thereto and specifically binds an analyte of interest or a conjugate of the analyte of interest, e.g., an antibody-analyte conjugate. As used herein, a "detectable label" is a compound or composition that produces or can be induced to produce a signal that is detectable by, e.g., visual, spectroscopic, photochemical, biochemical, immunochemical, or chemical means. The use of the term "labeled" as a modifier of a given substance, e.g., a labeled antibody, means that the substance has a detectable label attached thereto. A detectable label can be attached directly or indirectly by way of a linker (e.g., an amino acid linker or a chemical moiety). Examples of detectable labels include radioactive and non-radioactive isotopes (e.g., $^{125}I$, $^{18}F$, $^{13}C$, etc.), enzymes (e.g., β-galactosidase, peroxidase, etc.) and fragments thereof, enzyme substrates, enzyme inhibitors, coenzymes, catalysts, fluorophores (e.g., rhodamine, fluorescein isothiocyanate, etc.), dyes, chemiluminescers and luminescers (e.g., dioxetanes, luciferin, etc.), and sensitizers. A substance, e.g., antibody, having a detectable label means that a detectable label that is not linked, conjugated, or covalently attached to the substance, in its naturally-occurring form, has been linked, conjugated, or covalently attached to the substance by the hand of man. As used herein, the phrase "by the hand of man" means that a person or an object under the direction of a person (e.g., a robot or a machine operated or programmed by a person), not nature itself, has performed the specified act. Thus, the steps set forth in the claims are performed by the hand of man, e.g., a person or an object under the direction of the person.

In some embodiments, the antibody is one that specifically binds a three-dimensional epitope of the ERFE polypeptide of interest as present in the test sample. In some embodiments, the antibody that specifically binds a three-dimensional epitope was raised against the ERFE polypeptide of interest. In some embodiments, the ERFE polypeptide of interest is human erythroferrone. In some embodiments, the antibody was raised against a recombinantly produced human erythroferrone that comprises a FLAG-tag, and optionally comprises a trypsin-sensitive site. In some embodiments, the antibody was raised against rhERFE1 or rhERFE2. In some embodiments, the antibody is one that specifically binds a linear epitope of the ERFE polypeptide of interest. In some embodiments, the linear epitope comprises or consists of the amino acid sequence ELPRGPGESRAGPAARPP (SEQ ID NO: 1). In some embodiments, the linear epitope comprises the amino acid sequence GESRAG (SEQ ID NO: 2). In some embodiments, the linear epitope consists of the amino acid sequence GESRAG (SEQ ID NO: 2). In some embodiments, the linear epitope comprises or consists of LGSPEPGAPSRSRAR (SEQ ID NO: 34).

In some embodiments, the test sample is contacted with a first antibody and a second antibody, both of which specifically bind the ERFE polypeptide of interest. In some embodiments, the ERFE polypeptide of interest is human erythroferrone. In some embodiments, the ERFE polypeptide of interest is an analog of human erythroferrone, such as macaque erythroferrone. In some embodiments, the antibody was raised against a recombinantly produced human erythroferrone that comprises a FLAG-tag, and optionally comprises a trypsin-sensitive site. In some embodiments, the antibody was raised against rhERFE1 or rhERFE2. In some embodiments, one of the antibodies specifically binds a three-dimensional epitope of the ERFE polypeptide of interest as present in the test sample and the other antibody specifically binds a linear epitope of the ERFE polypeptide of interest. In some embodiments, the linear epitope comprises or consists of the amino acid sequence ELPRGPGESRAGPAARPP (SEQ ID NO: 1). In some embodiments, the linear epitope comprises the amino acid sequence GESRAG (SEQ ID NO: 2). In some embodiments, the linear epitope consists of the amino acid sequence GESRAG (SEQ ID NO: 2). In some embodiments, the linear epitope comprises or consists of LGSPEPGAPSRSRAR (SEQ ID NO: 34). In some embodiments, the first antibody and/or the second antibody are raised against the ERFE polypeptide of interest. In some embodiments, the first antibody is used as a capture reagent and the second antibody has a detectable label conjugated thereto. In some embodiments, both the first antibody and the second antibody have detectable labels conjugated thereto and a third antibody that specifically binds the first antibody and/or the second antibody is used as a capture reagent.

The capture reagent may be immobilized on an assay substrate. The capture reagent may be immobilized on the assay substrate before and/or after binding the analyte of interest. As used herein, an "assay substrate" refers to any substrate that may be used to immobilize a capture reagent thereon. Examples of assay substrates include membranes (e.g., a nitrocellulose membrane, a polyvinylidene fluoride (PVDF) membrane, a cellulose acetate membrane, etc.), beads, slides, multi-well plates, and the like. One skilled in the art may readily select an appropriate assay substrate for a given assay format, number of samples to be tested, and detectable label.

The assay substrate may be incubated with a blocking buffer before and/or after the capture reagent is immobilized thereon. In some embodiments, the blocking buffer comprises serum albumin, such as bovine serum albumin (BSA) or human serum albumin. In some embodiments, the blocking buffer comprises casein and/or fragments thereof. In some embodiments, the blocking buffer comprises both serum albumin and casein (or casein fragments). In some embodiments, the blocking buffer comprises PBS, 0.2% Na casein, 0.05% Tween 20, and 0.1M NaCl.

In some embodiments, the assay substrate containing the capture reagent immobilized thereon is then contacted with the sample to be tested under conditions that allow the capture reagent to form a complex with the analyte of interest. For example, an assay substrate having immobilized thereon a first antibody that specifically binds a given erythroferrone of interest is physically contacted with a serum sample under conditions that allow the first antibody to specifically bind the erythroferrone, if present in the serum sample, and then washed to remove any unbound molecules. The assay substrate is then incubated with a detection reagent under conditions that allow the detection reagent to specifically bind the analyte of interest or conjugates of the analyte of interest, e.g., conjugates comprising the analyte of interest and the capture reagent. For example, after contact with the serum sample, the assay substrate is incubated with a second antibody that has a detectable label and specifically binds any erythroferrone conjugated to first antibody. After contact with the detection reagent, the assay substrate may be washed to remove any unbound molecules. Then any detectable label that is present can be detected and/or measured using methods in the art.

In some embodiments, the immunoassays of the present invention are in the format of a sandwich ELISA, in which a first antibody that specifically binds the ERFE polypeptide of interest is immobilized on an assay substrate. The assay substrate having the first antibody immobilized thereon is then incubated with a sample to be tested for a suitable period under conditions that allow for the formation of an antibody-analyte complex. Such a complex can then be detected using a second antibody that specifically binds the ERFE polypeptide of interest. The second antibody can be conjugated to a detectable label, which can release a signal directly or indirectly. The intensity of the signal may represent the level of the ERFE polypeptide of interest in the sample. In some embodiments, both the first antibody and the second antibody have a detectable label attached thereto and a third antibody that specifically binds the first antibody and/or the second antibody is used as a capture reagent. In some embodiments, the detection reagent is first mixed with the sample to be tested and then the mixture is contacted with an assay substrate having a capture reagent immobilized thereon. In some embodiments, the ERFE polypeptide of interest is human erythroferrone. In some embodiments, one or both antibodies were raised against a recombinantly produced human erythroferrone that comprises a FLAG-tag, and optionally comprises a trypsin-sensitive site. In some embodiments, one or both antibodies were raised against rhERFE1 or rhERFE2. In some embodiments, one of the antibodies specifically binds a three-dimensional epitope of the ERFE polypeptide of interest as present in the test sample and the other antibody specifically binds a linear epitope of the ERFE polypeptide of interest. In some embodiments, the linear epitope comprises or consists of the amino acid sequence ELPRGPGESRAGPAARPP (SEQ ID NO: 1). In some embodiments, the linear epitope comprises the amino acid sequence GESRAG (SEQ ID NO: 2). In some embodiments, the linear epitope consists of the amino acid sequence GESRAG (SEQ ID NO: 2). In some embodiments, the linear epitope comprises or consists of LGSPEPGAPSRSRAR (SEQ ID NO: 34). In some embodiments, the first antibody and/or the second antibody are raised against the ERFE polypeptide of interest.

Diagnostic and Prognostic Applications

The methods and kits according to the present invention may be used in the evaluation of an iron metabolism disease, preferably a disease or condition related to abnormally low levels of erythroferrone or a disease or condition related to abnormally high levels of erythroferrone. The methods and kits of the present invention may be used to monitor the progress of such a disease, assess the efficacy of a treatment for the disease, and/or identify patients suitable for a given treatment in a subject. The methods and kits of the present invention may be used to diagnose a subject as having an iron metabolism disease and/or provide the subject with a prognosis.

In some embodiments, an immunoassay according to the present invention may be used to determine whether a subject exhibits a level of erythroferrone that is low or high as compared to a control. In some embodiments, the control is a sample from a normal, healthy subject. In some embodiments, the control is a pooled sample from a plurality of normal, healthy subjects. In some embodiments, the control is a given reference level. For example, in some embodiments, the given reference level is 30 ng/ml and a concentration level above 30 ng/ml is identified as a high level. The high level may then be used to diagnose the subject as suffering from a disease or condition related to abnormally high levels of erythroferrone.

The assays exemplified herein exhibit a limit of detection (LOD) of 12 ng/ml.

Therefore, in some embodiments, the sample to be tested is concentrated and then the level of erythroferrone is measured in the concentrated sample and the level of erythroferrone in the unconcentrated sample is mathematically extrapolated from the degree of concentration.

Because normal levels of erythroferrone can be below the LOD, in some embodiments, a subject can be diagnosed as having a low level of erythroferrone, by increasing the level of erythroferrone in the subject by, for example, administering a given amount of erythropoietin and then measuring the level of erythroferrone after a given time after erythropoietin administration and then comparing the level to a control. In these embodiments, the control may be a sample taken from a normal, healthy subject after the same given time after administration of the same given amount of erythropoietin, a pooled sample from a plurality of normal, healthy subjects whose samples were taken after the same given time after administration of the same given amount of erythropoietin, or a given reference value which is an average level determined from a plurality of normal, healthy subjects whose samples were taken after the same given time after administration of the same given amount of erythropoietin. If the increased level is lower than the control, the level can be identified as a low level. The low level may then be used to diagnose the subject as suffering from a disease or condition related to abnormally low levels of erythroferrone.

A subject identified as having a low level or a high level may be subjected to a suitable treatment. For example, a subject identified as having a high level of erythroferrone or diagnosed as suffering from disease or condition related to abnormally high levels of erythroferrone may be treated with an antagonist of erythropoietin or with a mini-hepcidin or with a modified mini-hepcidin peptide such as those described in WO 2010/065815 and WO 2013/086143. As another example, a subject identified as having a low level of erythroferrone or diagnosed as suffering from a disease or condition related to abnormally low levels of erythroferrone may be treated with erythropoietin or an agonist of erythropoietin.

In some embodiments, the methods and kits according to the present invention may be used to monitor the efficacy of treatment with a therapeutic, e.g., erythropoietin, that modulates the level of erythroferrone produced in the subject and the dosage of the therapeutic may be adjusted accordingly.

Non-Clinical Applications

In some embodiments, the methods and kits according to the present invention may be used for research purposes. For example, the methods and kits according to the present invention may be used to identify diseases that are caused by abnormal levels of erythroferrone and/or identify diseases that result in abnormal levels of erythroferrone. In some embodiments, the methods and kits according to the present invention may be used to study mechanisms, e.g., mechanisms and pathways involving erythroferrone. In some embodiments, the methods and kits according to the present invention may be used to develop and screen for therapeutics that increase or decrease levels of erythroferrone in subjects.

In some embodiments, the methods and kits according to the present invention may be used for experiments to elucidate the pathophysiological interaction between erythropoiesis and iron homeostasis, including the pathogenesis of iron-loading anemias, erythropoietic response to therapy with erythropoiesis-stimulating agents in chronic kidney disease, anemia of cancer, anemia of inflammation, and physiological adaptations to hypoxia, altitude, or blood donation.

Kits

In some embodiments, the present invention provides kits for use in evaluating an ERFE polypeptide of interest, e.g., human erythroferrone or an analog thereof, in samples, e.g., biological samples from human patients. In some embodiments, the kits comprise a capture reagent that specifically binds the ERFE polypeptide of interest packaged together with a detection reagent for detecting and/or measuring any ERFE polypeptides conjugated with the capture reagent.

In some embodiments, kits according to the present invention comprise a first antibody that specifically binds a three-dimensional epitope of human erythroferrone packaged together with a second antibody that specifically binds a linear epitope of human erythroferrone. In some embodiments, the linear epitope comprises or consists of the amino acid sequence ELPRGPGESRAGPAARPP (SEQ ID NO: 1). In some embodiments, the linear epitope comprises the amino acid sequence GESRAG (SEQ ID NO: 2). In some embodiments, the linear epitope consists of the amino acid sequence GESRAG (SEQ ID NO: 2). In some embodiments, the linear epitope comprises or consists of LGSPEPGAPSRSRAR (SEQ ID NO: 34). In some embodiments, the first antibody and/or the second antibody are raised against human erythroferrone.

Kits according to the present invention may further comprise an assay substrate for performing an immunoassay and immobilizing the capture reagent thereto. Kits according to the present invention may also comprise one or more reagents, e.g., blocking buffers, assay buffers, diluents, wash solutions, etc., for performing the immunoassay. Kits may optionally provide additional components such as interpretive information, control samples, and reference levels, and standards.

In some embodiments, the kits include a carrier, package, or container that may be compartmentalized to receive one or more containers, such as vials, tubes, and the like. In some embodiments, the kits optionally include an identifying description or label or instructions relating to its use. In some embodiments, the kits include information prescribed by a governmental agency that regulates the manufacture, use, or sale of compounds and compositions according to the present invention.

In some embodiments, the kits further comprise one or more erythroferrone therapeutics, optionally in one or more unit dosage forms, packaged together as a pack and/or in drug delivery device, e.g., a pre-filled syringe, for preventing, inhibiting, reducing, or treating an iron metabolism disease in a subject. As used herein, an "erythroferrone therapeutic" refers to a compound that increases or decreases the level of erythroferrone, e.g., erythropoietin, agonists of erythropoietin, antagonists of erythropoietin, or a compound that modulates iron uptake, e.g., hepcidin, mini-hepcidins, and modified mini-hepcidins, in a subject.

The following examples are intended to illustrate but not to limit the invention.

METHODS

Recombinant hERFE Production and Purification

The hERFE sequence was cloned into pcDNA3.1 with following modifications:

vector signal sequence (IL-2) was used instead of the native sequence, followed by a spacer (italics, SEQ ID NO: 4), a FLAG-tag (bolded, SEQ ID NO: 5), and a trypsin-sensitive site (dotted underline, SEQ ID NO: 6):

```
                                              (rhERFE1, SEQ ID No: 3)
MYRMQLLSCIALSLALVTNSIS AMVRS DYKDDDDK SPEPGAPSRSRARREPPPGNELPRGPGESRA

GPAARPPEPTAERAHSVDPRDAWMLFVRQSDKGVNGKKRSRGKAKKLKFGLPGPPGPPGPQGPPGP

IIPPEALLKEFQLLLLKGAVRQRERAEPEPCTCGPAGPVAASLAPVSATAGEDDDDVVGDVLALLAA

PLAPGPRAPRVEAAFLCRLRRDALVERRALHELGVYYLPDAEGAFRRGPGLNLTSGQYRAPVAGFY

ALAATLHVALGEPPRRGPPRPRDHLRLLICIQSRCQRNASLEAIMGLESSSELFTISVNGVLYLQM

GQWTSVFLDNASGCSLTVRSGSHFSAVLLGV
```

Because the FLAG tag was mostly lost during cell culture, the recombinant hERFE was further modified by removing the trypsin-sensitive site which allowed the protein to be secreted efficiently with its FLAG tag:

```
MYRMQLLSCIALSLALVTNSIS AMVRS DYKDDDDK SPEPPPPGNELPRGP

GESRAGPAARPPEPTAERAHSVDPRDAWMLFVRQSDKGVNGKKRSRGKAK

KLKFGLPGPPGPPGPQGPPGPIIPPEALLKEFQLLLLKGAVRQRERAEPEP

CTCGPAGPVAASLAPVSATAGEDDDDVVGDVLALLAAPLAPGPRAPRVEA

AFLCRLRRDALVERRALHELGVYYLPDAEGAFRRGPGLNLTSGQYRAPVA

GFYALAATLHVALGEPPRRGPPRPRDHLRLLICIQSRCQRNASLEAIMGL

ESSSELFTISVNGVLYLQMGQWTSVFLDNASGCSLTVRSGSHFSAVLLGV (rhERFE2, SEQ ID NO: 7)
```

FREESTYLE 293F cells (Life Technologies) were grown in shaking flask (250 rpm) at 37° C. in an 8% $CO_2$ humidified incubator to cell density $10^6$ ml in 100 ml of FREESTYLE 293 Expression medium, then transfected per manufacturer's instructions (Invitrogen Catalog #K9000-01) using 100 μg of rhERFE1 or rhERFE2 plasmid DNA and 200 μl 293FECTIN(Life Technologies). The transfected cells were reincubated in the shaking flaSk (250 rpm) at 37'C. in an 8% $CO_2$ humidified incubator for 3-5 days in 100 ml FREESTYLE 293 Expression medium supplemented with Protease Inhibitor Cocktail (Sigma) and the medium was collected. rhERFE1 was purified from supernatant using ion-exchange columns Macro-prep, Biorad) and eluted, by stepwise increasing concentrations of NaCl/$Na_2HPO_4$ buffer (0.1 to 1M, pH 7.5). rhERFE2 was purified using an anti-FLAG M2 affinity gel according to the manufacturer's protocol (Sigma), eluting with 100 μg/ml FLAG peptide (Sigma). NaCl/$Na_2HPO_4$ buffer and FLAG peptide were removed by filtration through Amicon Ultra 30K device (Millipore) and recombinant ERFE resuspended in saline (0.9% NaCl). The purified protein was electrophoretically heterogeneous, indicating posttranslational processing and multimerization characteristic of the TNFα-Clq family of proteins (see, reference #5). Predominant bands on reducing SDS-PAGE were at 52 kD and 26 kD. Antigen concentration was estimated by absorbance (1 mg/ml) at 280 nm=0.57.

Rabbit Monoclonal Antibody Production

Rabbit hybridomas were generated (custom order fulfilled by Abcam, Burlingame, Calif.) from rabbits immunized by rhERFE1 and boosted by rhERFE2. Hybridoma supernatants were selected for reactivity against rhERFE2. After biotinylation of Mabs (EZ-Link sulfo-NHS-LC-LC-Biotin kit, Thermo Fisher Scientific), optimal pair of unbiotinylated capture Mab and biotinylated detection Mab was chosen by checkerboard testing with rhERFE1 and rhERFE2. The cDNAs encoding the final Mab pair (#9 and #42) were cloned from the hybridomas and used to produce the Mabs recombinantly. Peptide epitope scanning showed that Mab #9 bound to the peptide ELPRGPGESRAGPAARPP (SEQ ID NO: 1) but not to 6 amino acid overlap neighbors suggesting that it was specific for an epitope centered on the underlined segment GESRAG (SEQ ID NO: 2). Mab #42 did not bind to linear peptides, indicating that it probably recognized a three-dimensional epitope.

The VH nucleotide sequence of Mab#9 is:

```
                                              (SEQ ID NO: 8)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGAATCGACCTCAATGACAAT

GCAATGAGATGGGTCCGCCAGGCTCCCGGGAAGGGGCTGGAATGGATCGG

AGTCATTTATATTGATACAAGCACATACTACGCGAGCTGGGCGAAAGGCC

GATTCACCATCTCCAAAACCTCGTCGACCACGGTGGATCTGAAAATCACC

AGTCCGACAACCGAGGACACGGCCACCTATTTCTGTGTCAGAGAGGATGG
```

TTATAGGCTTGGTGACGTCTGGGGCCCAGGCACCCTGGTCACCGTCTCCT

CAGGGCAACCTAAGGCTCCATCAGTCTTCCCACTGGCCCCCTGCTGCGGG

GACACACCCAGCTCCACGGTGACCCTGGGCTGCCTGGTCAAAGGGTACCT

CCCGGAGCCAGTGACCGTGACCTGGAACTCGGGCACCCTCACCAATGGGG

TACGCACCTTCCCGTCCGTCCGGCAGTCCTCAGGCCTCTACTCGCTGAGC

AGCGTGGTGAGCGTGACCTCAAGCAGCCAGCCCGTCACCTGCAACGTGGC

CCACCCAGCCACCAACACCAAAGTGGACAAGACCGTTGCGCCCTCGACAT

GCAGCAAGCCCACGTGCCCACCCCCTGAACTCCTGGGGGGACCGTCTGTC

TTCATCTTCCCCCCAAAACCCAAGGACACCCTCATGATCTCACGCACCCC

CGAGGTCACATGCGTGGTGGTGGACGTGAGCCAGGATGACCCCGAGGTGC

AGTTCACATGGTACATAAACAACGAGCAGGTGCGCACCGCCCGGCCGCCG

CTACGGGAGCAGCAGTTCAACAGCACGATCCGCGTGGTCAGCACCCTCCC

CATCGCGCACCAGGACTGGCTGAGGGGCAAGGAGTTCAAGTGCAAAGTCC

ACAACAAGGCACTCCCGGCCCCCATCGAGAAAACCATCTCCAAAGCCAGA

GGGCAGCCCTGGAGCCGAAGGTCTACACCATGGGCCCTCCCCGGGAGGA

GCTGAGCAGCAGGTCGGTCAGCCTGACCTGCATGATCAACGGCTTCTACC

CTTCCGACATCTCGGTGGAGTGGGAGAAGAACGGGAAGGCAGAGGACAAC

TACAAGACCACGCCGGCCGTGCTGGACAGCGACGGCTCCTACTTCCTCTA

CAGCAAGCTCTCAGTGCCCACGAGTGAGTGGCAGCGGGGCGACGTCTTCA

CCTGCTCCGTGATGCACGAGGCCTTGCACAACCACTACACGCAGAAGTCC

ATCTCCCGCTCTCCGGGTAAATGA

The encoded VH polypeptide sequence of Mab#9 is:
(SEQ ID NO: 9)
METGLRWLLLVAVLKGVQCQSVEESGGRLVTPGTPLTLTCTVS<u>GIDLNDN</u>
<u>AMR</u>WVRQAPGKGLEWIGV<u>IYIDTST</u>YYASWAKGRFTISKTSSTTVDLKIT
SPTTEDTATYFC<u>VREDGYRLGDV</u>WGPGTLVTVSSGQPKAPSVFPLAPCCG
DTPSSTVTLGCLVKGYLPEPVTVTWNSGTLTNGVRTFPSVRQSSGLYSLS
SVVSVTSSSQPVTCNVAHPATNTKVDKTVAPSTCSKPTCPPPELLGGPSV
FIFPPKPKDTLMISRTPEVTCVVVDVSQDDPEVQFTWYINNEQVRTARPP
LREQQFNSTIRVVSTLPIAHQDWLRGKEFKCKVHNKALPAPIEKTISKAR
GQPLEPKVYTMGPPREELSSRSVSLTCMINGFYPSDISVEWEKNGKAEDN
YKTTPAVLDSDGSYFLYSKLSVPTSEWQRGDVFTCSVMHEALHNHYTQKS
ISRSPGK The predicted CDRs of the VH chain of Mab #9 are underlined above and are as follows: GIDLNDNA (CDR1, SEQ ID NO: 10), IYIDTST (CDR2, SEQ ID NO: 11), and VREDGYRLGDV (CDR3, SEQ ID NO: 12).

The VL nucleotide sequence of Mab#9 is:
(SEQ ID NO: 13)
ATGGACACGAGGGCCCCACTCAGCTGCTGGGGCTCCTGCTGCTCTGGCT

CCCAGATGCCAGATGTGCGCTTGTGATGACCCAGACTCCATCCTCCGTGT

CTGCAGGTGTGGGAGGCACAGTCACCATCAACTGCCAGGCCAGTCAGAGT

CTTTATAATAACAACTATTTATCCTGGTTTCAGCAGAAACCAGGGCAGCC

TCCCAAGCTCCTGATCTACTGGGCATCCACTCTGGCATCTGGGGTCCCAT

CCCGGTTCAGTGGCAGTGGATCTGGGACACAGTTCACTCTCACCATCAGT

GGCGTGGCGTGTGACGATGCTGCCACTTACTACTGTGCAGGCTATAAAAG

TAGTAGTAATGATGATTTTGCTTTCGGCGGAGGGACCGAGGTGGTGGTCA

AAGGTGATCCAGTTGCACCTACTGTCCTCATCTTCCCACCAGCTGCTGAT

CAGGTGGCAACTGGAACAGTCACCATCGTGTGTGTGGCGAATAAATACTT

TCCCGATGTCACCGTCACCTGGGAGGTGGATGGCACCACCCAAACAACTG

GCATCGAGAACCGTAAAACACCGCAGAATTCTGCAGATTGTACCTACAAC

CTCAGCAGCACTCTGACACTGACCAGCACACAGTACAACAGCCACAAAGA

GTACACCTGCAAGGTGACCCAGGGCACGACCTCAGTCGTCCAGAGCTTCA

ATAGGGGTGACTGTTAG

The encoded VL polypeptide sequence of Mab#9 is:
(SEQ ID NO: 14)
MDTRAPTQLLGLLLLWLPDARCALVMTQTPSSVSAGVGGTVTINCQAS<u>QS</u>
<u>LYNNNY</u>LSWFQQKPGQPPKLLIY<u>WAS</u>TLASGVPSRFSGSGSGTQFTLTIS
GVACDDAATYYC<u>AGYKSSSNDDFA</u>FGGGTEVVVKGDPVAPTVLIFPPAAD
QVATGTVTIVCVANKYFPDVTVTWEVDGTTQTTGIENRKTPQNSADCTYN
LSSTLTLTSTQYNSHKEYTCKVTQGTTSVVQSFNRGDC The predicted CDRs of the VL chain of Mab #9 are underlined above and are as follows: QSLYNNNY (CDR1, SEQ ID NO: 15), WAS (CDR2, SEQ ID NO: 16), and AGYKSSSNDDFA (CDR3, SEQ ID NO: 17).

The VH nucleotide sequence of Mab#42 is:
(SEQ ID NO 18)
ATGGAGACTGGGCTGCGCTGGCTTCTCCTGGTCGCTGTGCTCAAAGGTGCC

CAGTGCCAGTCGCTGGAGGAGTCCGGGGGTCGCCTGGTAACGCCTGGAGGA

TCCCTGACACTCACCTGCACAGTCTCTGGAATCGACCTCAGTAGCTATGAA

ATGGGCTGGGTCCGCCAGGCTCCAGGGAAGGGGCTGGAATGGATCGGAGTA

ATTGGTACTGATGGTACCGCAGTCTACGCGACCTGGGTGAAAGGCCGATTC

ACCATCTCCAAAACCTCGACCACGGTGGATCTGAAAATGACCAGTCTGACA

ACCGAGGACACGGCCACCTATTTCTGTGCCCGAGATTCTTCTGGTAATAGT

AATTATAGGGCTTTTGATCCCTGGGGCCCAGGCACCCTGGTCACCGTCTCC

TCAGGGCAACCTAAGGCTCCATCAGTCTTCCCACTGGCCCCCTGCTGCGGG

GACACACCCAGCTCCACGGTGACCCTGGGCTGCCTGGTCAAAGGGTACCTC

CCGGAGCCAGTGACCGTGACCTGGAACTCGGGCACCCTCACCAATGGGGTA

CGCACCTTCCCGTCCGTCCGGCAGTCCTCAGGCCTCTACTCGCTGAGCAGC

GTGGTGAGCGTGACCTCAAGCAGCCAGCCCGTCACCTGCAACGTGGCCCAC

CCAGCCACCAACACCAAAGTGGACAAGACCGTTGCGCCCTCGACATGCAGC

AAGCCCACGTGCCCACCCCCTGAACTCCTGGGGGGACCGTCTGTCTTCATC

TTCCCCCCAAAACCCAAGGACACCCTCATGATCTCACGCACCCCCGAGGTC

ACATGCGTGGTGGTGGACGTGAGCCAGGATGACCCCGAGGTGCAGTTCACA

TGGTACATAAACAACGAGCAGGTGCGCACCGCCCGGCCGCCGCTACGGGAG

CAGCAGTTCAACAGCACGATCCGCGTGGTCAGCACCCTCCCCATCGCGCAC

CAGGACTGGCTGAGGGGCAAGGAGTTCAAGTGCAAAGTCCACAACAAGGCA

CTCCCGGCCCCCATCGAGAAAACCATCTCCAAAGCCAGAGGGCAGCCCCTG

GAGCCGAAGGTCTACACCATGGGCCCTCCCCGGGAGGAGCTGAGCAGCAGG

TCGGTCAGCCTGACCTGCATGATCAACGGCTTCTACCCTTCCGACATCTCG

GTGGAGTGGGAGAAGAACGGGAAGGCAGAGGACAACTACAAGACCACGCCG

GCCGTGCTGGACAGCGACGGCTCCTACTTCCTCTACAGCAAGCTCTCAGTG

CCCACGAGTGAGTGGCAGCGGGGCGACGTCTTCACCTGCTCCGTGATGCAC

GAGGCCTTGCACAACCACTACACGCAGAAGTCCATCTCCCGCTCTCCGGGT

AAATGA

The encoded VH polypeptide sequence of Mab#42 is:
(SEQ ID NO 19)
METGLRWLLLVAVLKGAQCQSLEESGGRLVTPGGSLTLTCTVS<u>GIDLSSYE</u>

MGWVRQAPGKGLEWIGV<u>IGTDGTA</u>VYATWVKGRFTISKTSTTVDLKMTSLT

TEDTATYFC<u>ARDSSGNSNYRAFDP</u>WGPGTLVTVSSGQPKAPSVFPLAPCCG

DTPSSTVTLGCLVKGYLPEPVTVTWNSGTLTNGVRTFPSVRQSSGLYSLSS

VVSVTSSSQPVTCNVAHPATNTKVDKTVAPSTCSKPTCPPPELLGGPSVFI

FPPKPKDTLMISRTPEVTCVVVDVSQDDPEVQFTWYINNEQVRTARPPLRE

QQFNSTIRVVSTLPIAHQDWLRGKEFKCKVHNKALPAPIEKTISKARGQPL

EPKVYTMGPPREELSSRSVSLTCMINGFYPSDISVEWEKNGKAEDNYKTTP

AVLDSDGSYFLYSKLSVPTSEWQRGDVFTCSVMHEALHNHYTQKSISRSPG

K

The predicted CDRs of the VH chain of Mab #42 are underlined above and are as follows: GIDLSSYE (CDR1, SEQ ID NO: 20), IGTDGTA (CDR2, SEQ ID NO: 21), and ARDSSGNSNYRAFDP (CDR3, SEQ ID NO: 22).

The VL nucleotide sequence of Mab#42 is:
(SEQ ID NO: 23)
ATGGACACGAGGGCCCCCACTCAGCTGCTGGGGCTCCTGCTGCTCTGGCTC

CCAGGTGCCAGATGTGCCTATGATATGACCCAGACTCCAGCCTCTGTGGAG

GTAGCTGTGGGAGGCACAGTCACCATCAAGTGCCAGGCCAGTCAGAGCATT

TACAGCTACTTATCCTGGTATCAGCAGAAACCAGGGCAGCCTCCCAAGCTC

CTGATCTACAGGGCATCCACTCTGGCATCTGGGGTCCCATCGCGGTTCAAA

GGCAGTGGATCTGGGACACAGTTCACTCTCACCATAAGCGACCTGGAGTGT

GCCGATGCTGCCACTTACTACTGTCAACAGGGTTTTGTTATTAGTAATGTT

CTTAATTCTTTCGGCGGAGGGACCGAGGTGGTGGTCAAAGGTGATCCAGTT

GCACCTACTGTCCTCATCTTCCCACCAGCTGCTGATCAGGTGGCAACTGGA

ACAGTCACCATCGTGTGTGTGGCGAATAAATACTTTCCCGATGTCACCGTC

ACCTGGGAGGTGGATGGCACCACCCAAACAACTGGCATCGAGAACAGTAAA

ACACCGCAGAATTCTGCAGATTGTACCTACAACCTCAGCAGCACTCTGACA

CTGACCAGCACACAGTACAACAGCCACAAAGAGTACACCTGCAAGGTGACC

CAGGGCACGACCTCAGTCGTCCAGAGCTTCAATAGGGGTGACTGTTAG

The encoded VL polypeptide sequence of Mab#42 is:
(SEQ ID NO: 24)
MDTRAPTQLLGLLLLWLPGARCAYDMTQTPASVEVAVGGTVTIKCQAS<u>QSI YSY</u>LSWYQQKPGQPPKLLIY<u>RAS</u>TLASGVPSRFKGSGSGTQFTLTISDLEC ADAATYYC<u>QQGFVISNVLNS</u>FGGGTEVVVKGDPVAPTVLIFPPAADQVATG

TVTIVCVANKYFPDVTVTWEVDGTTQTTGIENSKTPQNSADCTYNLSSTLT

LTSTQYNSHKEYTCKVTQGTTSVVQSFNRGDC

The predicted CDRs of the VL chain of Mab #42 are underlined above and are as follows: QSIYSY (CDR1, SEQ ID NO: 25), RAS (CDR2, SEQ ID NO: 26), and QQGFVISNVLNS (CDR3, SEQ ID NO: 27).

In some embodiments, an antibody according to the present invention comprises GIDLNDNA (SEQ ID NO: 10), IYIDTST (SEQ ID NO: 11), VREDGYRLGDV (SEQ ID NO: 12), QSLYNNNY (SEQ ID NO: 15), WAS (SEQ ID NO: 16), and AGYKSSSNDDFA (SEQ ID NO: 17). In some embodiments, an antibody according to the present invention comprises GIDLSSYE (SEQ ID NO: 20), IGTDGTA (SEQ ID NO: 21), ARDSSGNSNYRAFDP (SEQ ID NO: 22), QSIYSY (SEQ ID NO: 25), RAS (SEQ ID NO: 26), and QQGFVISNVLNS (SEQ ID NO: 27).

In some embodiments, the VH sequence of an antibody according to the present invention comprises GIDLNDNA (SEQ ID NO: 10), IYIDTST (SEQ ID NO: 11), and VREDGYRLGDV (SEQ ID NO: 12). In some embodiments, the VH sequence of an antibody according to the present invention comprises GIDLSSYE (SEQ ID NO: 20), IGTDGTA (SEQ ID NO: 21), and ARDSSGNSNYRAFDP (SEQ ID NO: 22). The VH polypeptide sequences of Mab #9 and Mab #42 have significant sequence identity. Therefore, in some embodiments, the VH sequence of an antibody according to the present invention comprises (SEQ ID NO: 28)
METGLRWLLLVAVLKG(X1)QCQS(X2)EESGGRLVTPG(X3)(X4)LTLT

CTVSGIDL(X5)(X6)(X7)(X8)M(X9)WVRQAPGKGLEWIGVI(X10)

(X11)D(X12)(X13)(X14)(X15)YA(X16)W(X17)KGRFTISKTS (X18)TTVDLK(X19)TS(X20)TTEDTATYFC(X21)R(X22)(X23)

(X24)(X25)(X26)(X27)(X28)YR(X29)(X30)D(X31)

wherein each X1 to X31 is independently any amino acid, and X18, X24, X25, X26, and X27 are each independently present or absent. In some embodiments, X1 is V or A, X2 is V or L, X3 is T or G, X4 is P or S, X5 is N or S, X6 is D or S, X7 is N or Y, X8 is A or E, X9 is R or G, X10 is Y or G, X11 is I or T, X12 is T or G, X13 is S or T, X14 is T or A, X15 is Y or V, X16 is S or T, X17 is A or V, X18 is S or absent, X19 is I or M, X20 is P or L, X21 is V or A, X22 is E or D, X23 is D or S, X24 is S or absent, X25 is G or absent, X26 is N or absent, X27 is S or absent, X28 is G or N, X29 is L or A, X30 is G or F, and/or X31 is V or P. In some embodiments, X1 is V or A, X2 is V or L, X3 is T or G, X4 is P or S, X5 is N or S, X6 is D or S, X7 is N or Y, X8 is A or E, X9 is R or G, X10 is Y or G, X11 is I or T, X12 is T or G, X13 is S or T, X14 is T or A, X15 is Y or V, X16 is S or T, X17 is A or V, X18 is S or absent, X19 is I or M, X20 is P or L, X21 is V or A, X22 is E or D, X23 is D or S, X24 is S or absent, X25 is G or absent, X26 is N or absent, X27 is S or absent, X28 is G or N, X29 is L or A, X30 is G or F, and X31 is V or P. In some embodiments, the antibody having SEQ ID NO: 28 contains GIDLNDNA (SEQ ID NO: 10), IYIDTST (SEQ ID NO: 11), and/or VREDGYRLGDV (SEQ ID NO: 12). In some embodiments, the antibody having SEQ ID NO: 28 contains GIDLSSYE (SEQ ID NO: 20), IGTDGTA (SEQ ID NO: 21), and/or ARDSSGNSNYRAFDP (SEQ ID NO: 22). In some embodiments, the VH sequence comprises a sequence having at least 79%, at least 80%, at least 81%, at least 82%, at least 83%, at least 84%, at least 85%, at least 86%, at least 87%, at least 88%, at least 88%, at least 89%, at least 90%, at least 91%, at least 91%, at least 92%, at least 93%, at least 94%, at least 95%, at least 96%, at least 97%, at least 98%, at least 99%, or 100% sequence identity to (SEQ ID NO: 29)
METGLRWLLLVAVLKGVQCQSVEESGGRLVTPGTPLTLTCTVSGIDLNDNA

MRWVRQAPGKGLEWIGVIYIDTSTYYASWAKGRFTISKTSSTTVDLKITSP

TTEDTATYFCVREDGYRLGDV
or (SEQ ID NO: 30)
METGLRWLLLVAVLKGAQCQSLEESGGRLVTPGGSLTLTCTVSGIDLSSYE

MGWVRQAPGKGLEWIGVIGTDGTAVYATWVKGRFTISKTSTTVDLKMTSLT

TEDTATYFCARDSSGNSNYRAFDP.

In some embodiments, the VH sequence comprises or consists of at least 79%, at least 80%, at least 81%, at least 82%, at least 83%, at least 84%, at least 85%, at least 86%, at least 87%, at least 88%, at least 88%, at least 89%, at least 90%, at least 91%, at least 91%, at least 92%, at least 93%, at least 94%, at least 95%, at least 96%, at least 97%, at least 98%, at least 99%, or 100% sequence identity to SEQ ID NO: 9 or SEQ ID NO: 19.

In some embodiments, the VL sequence of an antibody according to the present invention comprises QSLYNNNY (SEQ ID NO: 15), WAS (SEQ ID NO: 16), and AGYKSSSNDDFA (SEQ ID NO: 17). In some embodiments, the VL sequence of an antibody according to the present invention comprises QSIYSY (SEQ ID NO: 25), RAS (SEQ ID NO: 26), and QQGFVISNVLNS (SEQ ID NO: 27). The VL polypeptide sequences of Mab #9 and Mab #42 have significant sequence identity. Therefore, in some embodiments, the VL sequence of an antibody according to the present invention comprises (SEQ ID NO: 31)
MDTRAPTQLLGLLLLWLP(X32)ARCA(X33)(X34)MTQTP(X35)SV (X36)(X37)(X38)VGGTVTI(X39)CQASQS(X40)Y(X41)(X42)

(X43)YLSW(X44)QQKPGQPPKLLIY(X45)ASTLASGVPSRF(X46)

GSGSGTQFTLTIS(X47)(X48)(X49)C(X50)DAATYYC(X51)(X52)

(X53)(X54)(X55)(X56)SN(X57)(X58)(X59)(X60)

wherein each X32 to X60 is independently any amino acid, and X42 and X43 are each independently present or absent. In some embodiments, X32 is D or G, X33 is L or Y, X34 is V or D, X35 is S or A, X36 is S or E, X37 is A or V, X38 is G or A, X39 is N or K, X40 is N or I, X41 is N or S, X42 is N or absent, X43 is N or absent, X44 is F or Y, X45 is W or R, X46 is S or K, X47 is G or D, X48 is V or L, X49 is A or E, X50 is D or A, X51 is A or Q, X52 is G or Q, X53 is Y or G, X54 is K or F, X55 is S or V, X56 is S or I, X57 is D or V, X58 is D or L, X59 is F or N, and/or X60 is A or S. In some embodiments, X32 is D or G, X33 is L or Y, X34 is V or D, X35 is S or A, X36 is S or E, X37 is A or V, X38 is G or A, X39 is N or K, X40 is N or I, X41 is N or S, X42 is N or absent, X43 is N or absent, X44 is F or Y, X45 is W or R, X46 is S or K, X47 is G or D, X48 is V or L, X49 is A or E, X50 is D or A, X51 is A or Q, X52 is G or Q, X53 is Y or G, X54 is K or F, X55 is S or V, X56 is S or I, X57 is D or V, X58 is D or L, X59 is F or N, and X60 is A or S. In some embodiments, the antibody having SEQ ID NO: 31 contains QSLYNNNY (SEQ ID NO: 15) and/or AGYKSSSNDDFA (SEQ ID NO: 17). In some embodiments, the antibody having QSIYSY (SEQ ID NO: 25) and/or QQGFVISNVLNS (SEQ ID NO: 27). In some embodiments, the VL sequence comprises a sequence having at least 82%, at least 83%, at least 84%, at least 85%, at least 86%, at least 87%, at least 88%, at least 88%, at least 89%, at least 90%, at least 91%, at least 91%, at least 92%, at least 93%, at least 94%, at least 95%, at least 96%, at least 97%, at least 98%, at least 99%, or 100% sequence identity to (SEQ ID NO: 32)
MDTRAPTQLLGLLLLWLPDARCALVMTQTPSSVSAGVGGTVTINCQASQSL

YNNNYLSWFQQKPGQPPKLLIYWASTLASGVPSRFSGSGSGTQFTLTISGV

ACDDAATYYCAGYKSSSNDDFA.

In some embodiments, the VL sequence comprises or consists of at least 82%, at least 83%, at least 84%, at least 85%, at least 86%, at least 87%, at least 88%, at least 88%, at least 89%, at least 90%, at least 91%, at least 91%, at least 92%, at least 93%, at least 94%, at least 95%, at least 96%, at least 97%, at least 98%, at least 99%, or 100% sequence identity to SEQ ID NO: 14. In some embodiments, the VL sequence comprises a sequence having at least 79%, at least 80%, at least 81%, at least 82%, at least 83%, at least 84%, at least 85%, at least 86%, at least 87%, at least 88%, at least 88%, at least 89%, at least 90%, at least 91%, at least 91%, at least 92%, at least 93%, at least 94%, at least 95%, at least 96%, at least 97%, at least 98%, at least 99%, or 100% sequence identity to (SEQ ID NO: 33)
MDTRAPTQLLGLLLLWLPGARCAYDMTQTPASVEVAVGGTVTIKCQASQSI

YSYLSWYQQKPGQPPKLLIYRASTLASGVPSRFKGSGSGTQFTLTISDLEC

DAAATYYCQQGFVISNVLNS.

In some embodiments, the VL sequence comprises or consists of at least 79%, at least 80%, at least 81%, at least 82%, at least 83%, at least 84%, at least 85%, at least 86%, at least 87%, at least 88%, at least 88%, at least 89%, at least 90%, at least 91%, at least 91%, at least 92%, at least 93%, at least 94%, at least 95%, at least 96%, at least 97%, at least 98%, at least 99%, or 100% sequence identity to SEQ ID NO: 23.

In some embodiments, an antibody according to the present invention comprises a VH sequence according to paragraph [0096] and a VL sequence according to paragraph [0097].

In some embodiments, the present invention provides a method of making an antibody that specifically binds human erythroferrone and/or an ERFE polypeptide, which comprises injecting a non-human animal with the ERFE polypeptide. In some embodiments, the ERFE polypeptide comprises or consists of the amino acid sequence GESRAG (SEQ ID NO: 2). In some embodiments, the ERFE polypeptide comprises or consists of the amino acid sequence ELPRGPGESRAGPAARPP (SEQ ID NO: 1). In some embodiments, the ERFE polypeptide comprises or consists of rhERFE1 (SEQ ID NO: 3). In some embodiments, the ERFE polypeptide comprises or consists of rhERFE2 (SEQ ID NO: 7). In some embodiments, the method further comprises making a hybridoma using the lymphocytes of the non-human animal, which was injected with the ERFE polypeptide and expresses antibodies against the human erythroferrone and/or an ERFE polypeptide, to obtain a monoclonal antibody that specifically binds the ERFE polypeptide. In some embodiments, the non-human animal is a rabbit.

In some embodiments, the present invention provides a method of making a recombinant antibody that specifically binds human erythroferrone and/or an ERFE polypeptide, which comprises recombinantly expressing a VH sequence according to paragraph [0096] and a VL sequence according to paragraph [0097].

Human ERFE Immunoassay 96-well high binding plates (Costar #3590) were coated with Mab #9 diluted to 1 µg/ml in sodium carbonate buffer (50 mM, pH 9.6), overnight at 4° C. Plates were washed 3-times with TBs-T (TBS+0.05% Tween 2.0) then blocked for 1 hour at room temperature with 200 µl/well Blocking Buffer (BB PBS, 0.2% Na casein, 0.05% Tween 20, 0.1M NaCl). Recombinant hERFE2 standard was first diluted to 1 µg/ml and then serially diluted in BB to 10, 5, 2.5, 1.25, and 0.625 ng/ml. After a 1 hour incubation at 25° C. in a 300 rpm shaker, the plate was washed 4-times with TBS-T, 0.10 seconds, 25° C., and 300 rpm per wash and incubated 1 hour at 25° C. 300 rpm in shaker with 100 µl/well biotinylated Mab #42 (1 µg/ml BB) After incubation for 1 hour at 25° C., 300 rpm in shaker, the plate was washed 4-times as before, incubated for 45 minutes with NEUTRAVIDIN HRP conjugate (ThermoScientific #31030) 1/5000 (100 µl/well) washed again 3-times as before and developed with 100 µl TMB Substrate System for ELISA (ThermoScientific #34028) at room temperature in the dark for 10 minutes. The reaction was stopped by adding 50 µl of 2N sulfuric acid and the plates were read on a SPECTRAMAX 250 (Molecular Devices) at 450 nm.

Hepcidin Assay

Hepcidin was measured by competitive ELISA using methods in the art. See, e.g., reference #6.

Human Samples

All human studies were approved by Institutional Review Boards at respective institutions and at UCLA.

Blood donors—Male blood donors at the New York Blood Center (n=30, age 19-65 years) donated 2 units of packed erythrocytes by apheresis. Samples were collected prior to and 2, 4, 7, 9, 11, 14 and 112 days following donation. Samples from female blood donors (n=30, age 18-61) were obtained from Discovery Life Sciences, San Louis Obispo, Calif.

EPO administration—Four geriatric patients at UCLA with moderate anemia of unknown etiology were administered 20,000 units of EPO subcutaneously and serum collected over a 1-week time course.

β-thalassemia—Patients were recruited at the UCSF Benioff Children's Hospital Oakland and included non-transfused (n=11, 10 M, 1F, average 35.7 years) or transfusion-dependent patients immediately before (n=10, 5 M, 5 F, 23 years) or 2-14 days after transfusion (n=13, 9 M, 4 F, 17.4 years).

Immunoassays for Other ERFE Polypeptides

At least Mab #9 was found to bind macaque erythroferrone. BLAST sequence alignments between human erythroferrone (Accession AHL84165.1) and macaque erythroferrone (i.e., *Macaca fascicularis* (Accession XP_015288524.1), *Macaca mulatta* (Accession XP_001094581.2), and *Macaca nemestrina* (Accession XP_011726193.1)) show that macaque erythroferrone contains 100% sequence identity to a portion of the linear epitope ELPRGPGESRAGPAARPP (SEQ ID NO: 1). Specifically, all three macaque sequences contain LGSPEPGAPSRSRAR (SEQ ID NO: 34). Therefore, in some embodiments, the antibody or the immunologically active portion thereof specifically binds a macaque erythroferrone, a protein comprising LGSPEPGAPSRSRAR (SEQ ID NO: 34), or LGSPEPGAPSRSRAR (SEQ ID NO: 34). Thus, in some embodiments, ERFE polypeptide being detected is a macaque erythroferrone, a protein comprising LGSPEPGAPSRSRAR (SEQ ID NO: 34), or LGSPEPGAPSRSRAR (SEQ ID NO: 34). In some embodiments, ERFE polypeptide being detected is a macaque erythroferrone, a protein comprising LGSPEPGAPSRSRAR (SEQ ID NO: 34), or LGSPEPGAPSRSRAR (SEQ ID NO: 34) and the capture reagent or the detection reagent is an antibody according to paragraphs [0083] to [0099] or an immunologically active portion thereof.

Additionally, because macaque erythroferrone has at least 91% sequence identity to human erythroferrone, Mab #42 is also expected to specifically bind macaque erythroferrone. Therefore, in some embodiments, the ERFE polypeptide being detected is a macaque erythroferrone, a protein comprising LGSPEPGAPSRSRAR (SEQ ID NO: 34), or LGSPEPGAPSRSRAR (SEQ ID NO: 34) and the capture reagent and the detection reagent are each independently an antibody according to paragraphs [0083] to [0099] or an immunologically active portion thereof.

Further BLAST searches of ERFE polypeptides containing the antigenic linear epitope GESRAG (SEQ ID NO: 2) reveal the following erythroferrone polypeptides have sequences containing SEQ ID NO: 2: *Aotus nancymaae* (Accession XP_021520750.1), *Cercocebus atys* (Accession XP)_011898406.1), *Equus caballus* (Accession XP_023498471.1), *Gorilla gorilla gorilla* (Accession XP_018877321.1), *Macaca fascicularis* (Accession XP_015288524.1), *Macaca mulatta* (Accession XP_001094581.2), *Macaca nemestrina* (Accession XP_011726193.1), *Microcebus murinus* (Accession XP_012611156.1), *Neomonachus schauinslandi* (Accession) XP_021534643.1), *Nomascus leucogenys* (Accession XP_012359931.1), *Odobenus rosmarus divergens* (Accession XP_012421343.1), *Pan troglodytes* (Accession XP_016806309.1 and XP_009442932.2), *Papio anubis* (Accession XP_009181726.1), *Piliocolobus tephrosceles* (Accession XP_023084478.1), *Pongo abelii* (Accession XP_024099321.1), *Rhinolophus sinicus* (Accession XP_019596439.1), and *Rhinopithecus roxellana* (Accession XP_010356276.1).

Therefore, in some embodiments, the ERFE polypeptide being detected is a protein that comprises or consists of comprises or consists of ELPRGPGESRAGPAARPP (SEQ ID NO: 1), GESRAG (SEQ ID NO: 2), or LGSPEPGAPSRSRAR (SEQ ID NO: 34). In some embodiments, the ERFE polypeptide being detected is an erythroferrone from an *Aotus* spp., a *Cercocebus* spp., an *Equus* spp., a *Gorilla* spp., *Homo sapiens*, a *Macaca* spp., a *Microcebus* spp., a *Neomonachus* spp., a *Nomascus* spp., an *Odobenus* spp., a *Pan* spp., a *Papio* spp., a *Piliocolobus* spp., a *Pongo* spp., a *Rhinolophus* spp., or a *Rhinopithecus* spp. In some embodiments, the ERFE polypeptide being detected is an erythroferrone from one of the following species: *Aotus nancymaae, Cercocebus atys, Equus caballus, Gorilla gorilla gorilla, Homo sapiens, Macaca fascicularis, Macaca mulatta, Macaca nemestrina, Microcebus murinus, Neomonachus schauinslandi, Nomascus leucogenys, Odobenus rosmarus divergens, Pan troglodytes, Papio anubis, Piliocolobus tephrosceles, Pongo abelii, Rhinolophus sinicus*, and *Rhinopithecus roxellana*. In some embodiments, the ERFE polypeptide being detected is human erythroferrone. In some embodiments, the ERFE polypeptide being detected is a macaque erythroferrone.

ADDITIONAL EMBODIMENTS

Embodiment 1. An immunoassay for detecting an ERFE polypeptide, preferably a human erythroferrone, in a sample, which comprises a1) contacting the sample with a capture reagent that specifically binds the ERFE polypeptide and then contacting with at least one detection reagent that specifically binds the ERFE polypeptide bound to the capture reagent, or a2) contacting the sample with at least one detection reagent that specifically binds the ERFE polypeptide and then contacting with a capture reagent that specifically binds the ERFE polypeptide bound to the at least one detection reagent; and b) detecting or measuring a detectable label of the at least one detection reagent.

Embodiment 2. The immunoassay of Embodiment 1, wherein the capture reagent or the at least one detection reagent is an antibody that specifically binds a three-dimensional epitope of the ERFE polypeptide.

Embodiment 3. The immunoassay of Embodiment 2, wherein the capture reagent or the at least one detection reagent is an antibody that specifically binds a linear epitope of the ERFE polypeptide.

Embodiment 4. The immunoassay of Embodiment 2, wherein the capture reagent is an antibody that specifically binds a linear epitope of the ERFE polypeptide and the at least one detection reagent is the antibody that specifically binds a three-dimensional epitope of the ERFE polypeptide.

Embodiment 5. The immunoassay of Embodiment 3 or 4, wherein the linear epitope comprises or consists of the amino acid sequence GESRAG (SEQ ID NO: 2).

Embodiment 6. The immunoassay of Embodiment 3 or 4, wherein the linear epitope comprises or consists of the amino acid sequence ELPRGPGESRAGPAARPP (SEQ ID NO: 1).

Embodiment 7. The immunoassay of Embodiment 2, wherein the antibody that specifically binds a three-dimensional epitope was raised against the human erythroferrone.

Embodiment 8. The immunoassay of Embodiment 2, wherein the antibody that specifically binds a three-dimensional epitope was raised against a recombinant human erythroferrone.

Embodiment 9. The immunoassay of Embodiment 8, wherein the recombinant human erythroferrone is rhERFE1 (SEQ ID NO: 3) or rhERFE2 (SEQ ID NO: 7).

Embodiment 10. The immunoassay according any one of the preceding Embodiments, which further comprises immobilizing the capture reagent to an assay substrate.

Embodiment 11. A method of determining whether the level of erythroferrone in a subject is low or high, which comprises performing the immunoassay according to any one of Embodiments 1 to 10 on a sample obtained from the subject to obtain a measured level of erythroferrone, and comparing the measured level of erythroferrone to a control.

REFERENCES

1. Finch C. Regulators of iron balance in humans. *Blood.* 1994; 84(6):1697-1702.
2. Kautz L, Jung G, Valore EV, Rivella S, Nemeth E, Ganz T. Identification of erythroferrone as an erythroid regulator of iron metabolism. &o NatGenet. 2014; 46(7):678-684.
3. Ganz T. Systemic iron homeostasis. *Physiol Rev.* 2013; 93(4):1721-1741.
4. Kautz L, Jung G, Du X, et al. Erythroferrone contributes to hepcidin suppression and iron overload in a mouse model of beta-thalassemia. *Blood.* 2015; 126(17):2031-2037.
5. Wang Y, Lam Karen SL, Yau M-h, Xu A. Post-translational modifications of adiponectin: mechanisms and functional implications. *Biochemical Journal.* 2008; 409(3):623-633.
6. Ganz T, Olbina G, Girelli D, Nemeth E, Westerman M. Immunoassay for human serum hepcidin. *Blood.* 2008; 112(10):4292-4297.

All scientific and technical terms used in this application have meanings commonly used in the art unless otherwise specified.

As used herein, the terms "subject", "patient", and "individual" are used interchangeably to refer to humans and non-human animals. The term "non-human animal" includes all vertebrates, e.g., mammals and non-mammals, such as non-human primates, horses, sheep, dogs, cows, pigs, chickens, and other veterinary subjects and test animals. In some embodiments of the present invention, the subject is a mammal. In some embodiments of the present invention, the subject is a human.

As used herein, "providing a diagnosis" and "diagnosing" refer to the physical and active step of informing, i.e., communicating verbally or by writing (on, e.g., paper or electronic media), another party, e.g., a patient, of the diagnosis. Similarly, "providing a prognosis" refers to the physical and active step of informing, i.e., communicating verbally or by writing (on, e.g., paper or electronic media), another party, e.g., a patient, of the prognosis.

The use of the singular can include the plural unless specifically stated otherwise. As used in the specification and the appended claims, the singular forms "a", "an", and "the" can include plural referents unless the context clearly dictates otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

The phrase "comprises or consists of" is used as a tool to avoid excess page and translation fees and means that in some embodiments the given thing at issue comprises something, and in some embodiments the given thing at issue consists of something. For example, the sentence "In some embodiments, the composition comprises or consists of A" is to be interpreted as if written as the following two separate sentences: "In some embodiments, the composition comprises A. In some embodiments, the composition consists of A." Similarly, a sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C."

To the extent necessary to understand or complete the disclosure of the present invention, all publications, patents, and patent applications mentioned herein are expressly incorporated by reference therein to the same extent as though each were individually so incorporated.

What is claimed is:

1. An antibody comprising a
   VH sequence that comprises GIDLNDNA (SEQ ID NO: 10), IYIDTST (SEQ ID NO: 11), and VREDGYRLGDV (SEQ ID NO: 12); and
   a VL sequence that comprises QSLYNNNY (SEQ ID NO: 15), WAS (SEQ ID NO: 16), and AGYKSSSNDDFA (SEQ ID NO: 17).

2. The antibody according to claim 1, wherein the antibody is a monoclonal antibody.

3. The antibody according to claim 1, wherein the antibody is an IgG isotype.

4. The antibody according to claim 1, wherein the antibody is a synthetic antibody.

5. A method of making the antibody according to claim 1, which comprises injecting a non-human animal with human erythroferrone, ELPRGPGESRAGPAARPP (SEQ ID NO: 1), GESRAG (SEQ ID NO: 2), LGSPEPGAPSRSRAR (SEQ ID NO: 34), SEQ ID NO: 3 (rhERFE1) and/or SEQ ID NO: 7 (rhERFE2).

6. An antibody comprising
   a VH sequence that comprises GIDLSSYE (SEQ ID NO: 20), IGTDGTA (SEQ ID NO: 21), and ARDSSGNSNYRAFDP (SEQ ID NO: 22), and
   a VL sequence that comprises QSIYSY (SEQ ID NO: 25), RAS (SEQ ID NO: 26), and QQGFVISNVLNS (SEQ ID NO: 27).

7. The antibody according to claim 6, wherein the antibody is a monoclonal antibody.

8. The antibody according to claim 6, wherein the antibody is an IgG isotype.

9. The antibody according to claim 6, wherein the antibody is a synthetic antibody.

10. A method of making the antibody according to claim 6, which comprises injecting a non-human animal with human erythroferrone, ELPRGPGESRAGPAARPP (SEQ ID NO: 1), GESRAG (SEQ ID NO: 2), LGSPEPGAPSRSRAR (SEQ ID NO: 34), SEQ ID NO: 3 (rhERFE1) and/or SEQ ID NO: 7 (rhERFE2).

11. An immunoassay for detecting an ERFE polypeptide in a sample, which comprises contacting the sample with an antibody according to claim 1 and detecting any resulting bound antibody with a detectable label.

12. An immunoassay for detecting an ERFE polypeptide in a sample, which comprises
    contacting the sample with an antibody according to claim 6 and detecting any resulting bound antibody with a detectable label.

13. An immunoassay for detecting an ERFE polypeptide in a sample, which comprises
    a1) contacting the sample with a capture reagent that specifically binds the ERFE polypeptide and then contacting with at least one detection reagent that specifically binds the ERFE polypeptide bound to the capture reagent, or
    a2) contacting the sample with at least one detection reagent that specifically binds the ERFE polypeptide and then contacting with a capture reagent that specifically binds the ERFE polypeptide bound to the at least one detection reagent; and
    b) detecting or measuring a detectable label of the at least one detection reagent bound to the ERFE polypeptide that is bound to the capture reagent, wherein the capture reagent is a first antibody and the at least one detection reagent is a second antibody, and wherein i) both the first antibody and the second antibody have a VH sequence that comprises GIDLNDNA (SEQ ID NO: 10), IYIDTST (SEQ ID NO: 11), and VREDGYRLGDV (SEQ ID NO: 12); and a VL sequence that comprises QSLYNNNY (SEQ ID NO: 15), WAS (SEQ ID NO: 16), and AGYKSSSNDDFA (SEQ ID NO: 17);

ii) both the first antibody and the second antibody have a VH sequence that comprises GIDLSSYE (SEQ ID NO: 20), IGTDGTA (SEQ ID NO: 21), and ARDSSGNSNYRAFDP (SEQ ID NO: 22) and a VL sequence that comprises QSIYSY (SEQ ID NO: 25), RAS (SEQ ID NO: 26), and QQGFVISNVLNS (SEQ ID NO: 27);

iii) the first antibody has a VH sequence that comprises GIDLNDNA (SEQ ID NO: 10), IYIDTST (SEQ ID NO: 11), and VREDGYRLGDV (SEQ ID NO: 12); and a VL sequence that comprises QSLYNNNY (SEQ ID NO: 15), WAS (SEQ ID NO: 16), and AGYKSSSNDDFA (SEQ ID NO: 17) and the second antibody has a VH sequence that comprises GIDLSSYE (SEQ ID NO: 20), IGTDGTA (SEQ ID NO: 21), and ARDSSGNSNYRAFDP (SEQ ID NO: 22) and a VL sequence that comprises QSIYSY (SEQ ID NO: 25), RAS (SEQ ID NO: 26), and QQGFVISNVLNS (SEQ ID NO: 27); or iv) the first antibody has a VH sequence that comprises GIDLSSYE (SEQ ID NO: 20), IGTDGTA (SEQ ID NO: 21), and ARDSSGNSNYRAFDP (SEQ ID NO: 22) and a VL sequence that comprises QSIYSY (SEQ ID NO: 25), RAS (SEQ ID NO: 26), and QQGFVISNVLNS (SEQ ID NO: 27) and the second antibody has a VH sequence that comprises GIDLNDNA (SEQ ID NO: 10), IYIDTST (SEQ ID NO: 11), and VREDGYRLGDV (SEQ ID NO: 12); and a VL sequence that comprises QSLYNNNY (SEQ ID NO: 15), WAS (SEQ ID NO: 16), and AGYKSSSNDDFA (SEQ ID NO: 17).

14. The immunoassay of claim 13, wherein (i) the capture reagent or the at least one detection reagent specifically binds a three-dimensional epitope of the ERFE polypeptide, (ii) the capture reagent or the at least one detection reagent specifically binds a linear epitope of the ERFE polypeptide, or (iii) the capture reagent specifically binds a linear epitope of the ERFE polypeptide and the at least one detection reagent specifically binds a three-dimensional epitope of the ERFE polypeptide.

15. The immunoassay of claim 14, wherein the linear epitope comprises or consists of the amino acid sequence ELPRGPGESRAGPAARPP (SEQ ID NO: 1), GESRAG (SEQ ID NO: 2), or LGSPEPGAPSRSRAR (SEQ ID NO: 34).

16. The immunoassay according to claim 13, wherein the first antibody and/or the second antibody was raised against the amino acid sequence of SEQ ID NO: 3 (rhERFE1) and/or SEQ ID NO: 7 (rhERFE2).

17. The immunoassay according claim 13, which further comprises immobilizing the capture reagent to an assay substrate.

18. The immunoassay according to claim 13, wherein the first antibody and/or the second antibody is a monoclonal antibody.

19. The immunoassay according to claim 13, wherein the first antibody and/or the second antibody is an IgG isotype.

20. The immunoassay according to claim 13, wherein the ERFE polypeptide is an analog of human erythroferrone.

21. The immunoassay according to claim 13, wherein the first antibody and/or the second antibody is a synthetic antibody.

22. A method of determining whether the level of an erythroferrone in a subject is low or high as compared to a control, which comprises performing the immunoassay according to claim 13 on a sample obtained from the subject to obtain a measured level of the erythroferrone, and comparing the measured level of the erythroferrone to a control.

23. The method of claim 22, which further comprises characterizing the subject as having an abnormally high level of the erythroferrone where the measured level of the erythroferrone is more than 30 ng/ml.

* * * * *